(12) United States Patent
Shadduck

(10) Patent No.: US 12,721,644 B2
(45) Date of Patent: Sep. 1, 2026

(54) MEDICAL SYSTEM AND METHOD OF USE

(71) Applicant: John H. Shadduck, Menlo Park, CA (US)

(72) Inventor: John H. Shadduck, Menlo Park, CA (US)

( * ) Notice: Subject to any disclaimer, the term of this patent is extended or adjusted under 35 U.S.C. 154(b) by 0 days.

(21) Appl. No.: 19/417,175

(22) Filed: Dec. 11, 2025

(65) Prior Publication Data

US 2026/0157768 A1 Jun. 11, 2026

Related U.S. Application Data

(60) Provisional application No. 63/737,010, filed on Dec. 20, 2024, provisional application No. 63/730,777, filed on Dec. 11, 2024.

(51) Int. Cl.

| | |
|---|---|
| ***A61B 17/3203*** | (2006.01) |
| ***A61B 1/307*** | (2006.01) |
| ***A61B 17/32*** | (2006.01) |
| *A61B 17/00* | (2006.01) |

(52) U.S. Cl.

CPC .......... *A61B 17/3203* (2013.01); *A61B 1/307* (2013.01); *A61B 17/320016* (2013.01); *A61B 2017/00057* (2013.01); *A61B 2017/32035* (2013.01)

(58) Field of Classification Search

CPC .......... A61B 17/3203; A61B 17/32037; A61B 17/320016; A61B 2018/00547; A61B 2017/00274; A61B 2017/00057; A61B 2017/32035; A61B 90/30; A61B 1/307

See application file for complete search history.

(56) References Cited

U.S. PATENT DOCUMENTS

| | | | |
|---|---|---|---|
| 6,375,635 | B1 | 4/2002 | Moutafis et al. |
| 6,508,816 | B2 | 1/2003 | Shadduck |
| 6,669,694 | B2 | 12/2003 | Shadduck |
| 6,911,028 | B2 | 6/2005 | Shadduck |
| 7,549,987 | B2 | 6/2009 | Shadduck |
| 7,674,259 | B2 | 3/2010 | Shadduck |
| 7,892,229 | B2 | 2/2011 | Shadduck et al. |
| 8,016,823 | B2 | 9/2011 | Shadduck |
| 8,187,269 | B2 | 5/2012 | Shadduck et al. |
| 8,313,485 | B2 | 11/2012 | Shadduck |
| 8,444,636 | B2 | 5/2013 | Shadduck et al. |
| 8,574,226 | B2 | 11/2013 | Shadduck |
| 8,579,888 | B2 | 11/2013 | Hoey et al. |
| 8,579,892 | B2 | 11/2013 | Hoey et al. |
| 8,579,893 | B2 | 11/2013 | Hoey |
| 8,721,632 | B2 | 5/2014 | Hoey et al. |
| 8,758,341 | B2 | 6/2014 | Shadduck |
| 8,858,549 | B2 | 10/2014 | Shadduck et al. |
| 8,900,223 | B2 | 12/2014 | Shadduck |
| 8,911,430 | B2 | 12/2014 | Hoey et al. |
| 9,113,944 | B2 | 8/2015 | Shadduck |
| 9,161,801 | B2 | 10/2015 | Hoey |
| 9,204,889 | B2 | 12/2015 | Shadduck |
| 9,364,250 | B2 | 6/2016 | Aljuri et al. |
| 9,433,457 | B2 | 9/2016 | Shadduck |

(Continued)

*Primary Examiner* — Tuan V Nguyen
(74) *Attorney, Agent, or Firm* — Levine Bagade Han LLP

(57) ABSTRACT

Systems and methods for resecting prostate tissue and applying thermal energy to prostate tissue before, during or after resection to prevent bleeding or coagulate bleeding in surfaces of prostate tissue in benign prostatic hyperplasia treatments.

25 Claims, 20 Drawing Sheets

(56) References Cited

U.S. PATENT DOCUMENTS

| | | | | |
|---|---|---|---|---|
| 9,468,487 | B2 | 10/2016 | Shadduck et al. | |
| 9,615,875 | B2 | 4/2017 | Shadduck | |
| 9,907,599 | B2 | 3/2018 | Hoey et al. | |
| 9,924,992 | B2 | 3/2018 | Hoey et al. | |
| 9,943,353 | B2 | 4/2018 | Hoey et al. | |
| 10,499,973 | B2 | 12/2019 | Hoey et al. | |
| 10,524,847 | B2 | 1/2020 | Shadduck | |
| 10,548,653 | B2 | 2/2020 | Hoey et al. | |
| 10,595,925 | B2 | 3/2020 | Hoey et al. | |
| 10,675,079 | B2 | 6/2020 | Shadduck | |
| 11,129,664 | B2 | 9/2021 | Shadduck et al. | |
| 11,141,210 | B2 | 10/2021 | Shadduck et al. | |
| 11,179,187 | B2 | 11/2021 | Shadduck et al. | |
| 11,207,118 | B2 | 12/2021 | Hoey et al. | |
| 11,284,931 | B2 | 3/2022 | Hoey et al. | |
| 11,284,932 | B2 | 3/2022 | Shadduck et al. | |
| 11,413,086 | B2 | 8/2022 | Hoey et al. | |
| 11,457,969 | B2 | 10/2022 | Hoey et al. | |
| 11,478,291 | B2 | 10/2022 | Shadduck et al. | |
| 11,672,584 | B2 | 6/2023 | Hoey et al. | |
| 2009/0254075 | A1* | 10/2009 | Paz | A61B 17/3203 606/28 |
| 2010/0145326 | A1* | 6/2010 | Hoey | A61B 18/1485 606/159 |
| 2020/0360100 | A1* | 11/2020 | Mantri | A61B 34/37 |
| 2022/0117651 | A1* | 4/2022 | Staid | A61B 17/3203 |

* cited by examiner

110'

110'

MEDICAL SYSTEM AND METHOD OF USE

RELATED APPLICATION INFORMATION

This application is a non-provisional of U.S. Provisional application no. 63/730,777 filed Dec. 11, 2024 and U.S. Provisional application no. 63/737,010 filed Dec. 20, 2024, the entirety of both of which are incorporated by reference.

FIELD OF THE INVENTION

The present invention is related to robotic surgical systems and methods for volumetric removal of prostate tissue to treat benign prostatic hyperplasia.

BACKGROUND OF THE INVENTION

Benign prostatic hyperplasia (BPH) is a prevalent condition among elderly men with increasing prevalence as men age and affects upwards of 60% of men by the age of 65. BPH consists of the progressive benign enlargement of the prostate gland, primarily attributable to unregulated hyperplastic growth in the epithelial and fibromuscular tissues of the transition zone and periurethral area of a human prostate, resulting that restricts flow from the bladder through the prostatic urethra.

Surgical interventions are a viable option in treating BPH with transurethral resection of prostate (TURP), historically regarded as a gold standard for small to moderately sized prostates. In a TURP procedure, a substantial volume of the patient's prostate gland is resected with an RF electrosurgical loop (a resectoscope), and the extraction of tissue reduces pressure on the prostatic urethra. The electrosurgical devices used in TURP procedures have the advantage of cauterizing the surface of the resected tissue, so post-treatment bleeding is not an issue. Other minimally invasive surgical treatments and implants for treating BPH are known in the prior art. However, volumetric resection, as in TURP procedure, provides the most immediate relief BPH symptoms. A significant disadvantage of a TURP resection is that the procedure is skill-dependent and requires 60 to 90 minutes in the operating room, making it a very costly treatment.

Water jet cutting in surgical applications. Water jet cutting technology has gained significant traction in many industries, including surgical applications. High-pressure water jet systems have demonstrated efficacy in surgical procedures by offering precise and controlled tissue cutting and obliteration.

However, these systems typically use high operating pressures, and to control the limits of the cutting effect, the high-pressure water jet is directed towards a backstop evacuation channel. Such surgical water jet devices are designed for precise, rapid removal of small volumes of tissue, often in confined spaces. The water jet carries kinetic energy that is focused on a narrow target area between a jet orifice and the backstop evacuation channel, allowing for controlling the boundaries of the cutting zone and avoiding the risk of collateral damage to tissue.

FIGS. 1A and 1B illustrate such prior working ends 10 and 12, where a surgical device has an elongate shaft with a working end configured with a high-pressure water jet that is directed towards a jet evacuation channel. FIG. 1A illustrates a water jet that propagates transverse to the axis of the shaft. FIG. 1B illustrates a water jet that propagates in alignment with the axis of the shaft from the jet orifice toward the backstop evacuation channel. FIGS. 1A and 1B illustrate devices commercialized by Hydrocision, Inc. and are used in spine discectomies and similar procedures. (FIGS. 1A and 1B are copied from Hydrocision's U.S. U.S. Pat. No. 6,375,635 at FIGS. 5*a* and 5*b* with the reference numbers removed for clarity).

The configurations of FIGS. 1A and B are optimized for precise, rapid removal of small volumes of tissue, such as herniated disc material. By confining the jet's energy between the jet orifice and the backstop evacuation channel, these water jet devices achieve highly localized tissue removal. However, these devices are not optimized for the volumetric removal of large tissue volumes, as required in BPH treatment. Further, such water jet devices are designed for resecting tissues that are not highly vascularized, such as disc tissue, as such water jet devices provide no mechanism for thermally cauterizing tissue.

Recently, a low-pressure variation of a water jet cutting device has been introduced for BPH treatments, for example, as disclosed in U.S. Pat. No. 9,364,250, owned by Procept Biorobotics. FIGS. 2A and 2B illustrate low-pressure water jet devices 14 and 16 (FIGS. 2A and 2B are copied from US. U.S. Pat. No. 9,364,250 at FIGS. 4 and 5 with the reference numbers removed for clarity). The device of FIGS. 2A-2B comprises a shaft adapted for trans-urethral introduction with a water jet that is pointed radially outward from the shaft towards prostate tissue instead of towards a backstop channel as in the surgical water jet devices of FIGS. 1A-1B. In FIGS. 2A-2B, it can be seen that the low-pressure water jet device is moved axially and rotationally to cut tissue. Since the water jet is directed radially outward from the shaft with no backstop, substantially low pressures are required compared to variations of FIGS. 1A and 1B. At some lower pressure levels, the water jets skeletonize tissue as the soft prostate glandular tissue is obliterated, but tougher tissue, such as blood vessel walls remains intact.

Directly aiming a high-pressure water jet at soft tissue presents significant challenges for predictable depth of cutting. The primary issue lies in the unpredictable nature of the jet-tissue interaction. Factors such as tissue heterogeneity (varying density and stiffness), variations in jet velocity and angle, and the dynamic nature of the cutting process make it difficult to achieve any predictable depth of tissue penetration. The high kinetic energy of the jet also can lead to unpredictable tissue displacement, deformation, and fragmentation, making it challenging to achieve a consistent and controlled resection.

In contrast, systems utilizing a backstop evacuation channel (FIGS. 1A-1B) entirely confines the water jet's energy to a controlled path and provides an exact cutting zone. This prior art approach with a backstop allows for complete control over the depth of tissue interaction and practically eliminates the risk of unintended damage to not-targeted tissues.

Another disadvantage to the low-pressure water jet in BPH procedures is the incidence of bleeding complications compared to other surgical modalities, such as TURP which resects and cauterized tissues contemporaneously with an RF cutting loop resectoscope. There remains a high degree of uncertainty regarding how bleeding should be managed during a low-pressure water jet procedure, but a combination of both electrocautery with a resectoscope and the use of traction devices has been reported to yield the best results. However, using an RF resectoscope adds significant unneeded costs to a low-pressure water jet procedure, as well as adding 15 to 30 minutes to the procedure time.

Similarly, new traction devices add to the cost of disposable devices needed for the procedure and add time to the procedure.

A BPH procedure using the commercial low-pressure water jet device requires about 60 minutes in the operating room. The low-pressure water jet is only actuated for 3 to 5 minutes in such a procedure to robotically move the jet axially and rotationally. The additional approximately 55 minutes of operating room time is needed for (i) mapping the prostate to determine the profile of the resection and (ii) using electrocautery devices and/or traction devices to stop bleeding in the resected cavity in the patient's prostate.

A need exists for a water jet cutting system that allows for very rapid, controlled tissue removal in a BPH procedure and that also provides rapid and effective cauterization of the surface of the resected cavity in the patient's prostate. The present invention aims to address this need by introducing a water jet cutting system capable of delivering controlled water jets that enable precise tissue resection without unwanted collateral damage and contemporaneous effective cauterization.

SUMMARY OF THE INVENTION

The present invention comprises a tissue resection system for treating BPH that robotically controls a single resection-cauterization device that is capable of very rapid volumetric resection, tissue extraction, and cauterization of surfaces of a resected cavity. Further, the system is supported by artificial intelligence (AI) and/or machine learning to ensure cauterization is provided during the resection step of the method. The resection is accomplished by adjustable dual liquid jets that use induced backstop turbulence as a backstop to control cutting depth. Cauterization is provided a vapor jet that undergoes a vapor-to-liquid phase transition in the treatment site to release and apply 540 cal/gm of energy in the phase change to, thereby instantly, thermally cauterize tissue in the interface of the condensation. The use of phase change energy released from a condensable water vapor to thermally ablate, cauterize or modify tissue is disclosed by the author in U.S. Pat. Nos. 7,674,259; 11,413,086; 11,207,118; 8,911,430; 8,721,632; 11,129,664; 9,615,875; 10,675,079; 8,579,888; 8,574,226; 8,579,893; 10,595,925; 8,900,223; 8,758,341; 11,284,931; 8,579,892; 11,179,187; 10,548,653; 9,204,889; 11,457,969; 10,499,973; 7,892,229; 9,468,487; 10,524,847; 9,433,457; 9,113,944; 8,313,485; 11,478,291; 9,907,599; 11,141,210; 7,549,987; 8,016,823; 8,444,636; 11,284,932; 9,924,992; 11,672,584, 9,161,801; 9,943,353; 8,858,549; 6,669,694; 8,187,269; 6,911,028 and 6,508,816.

An exemplary resection-cauterization device or probe comprises a proximal hub coupled to an elongated shaft that is adapted for trans-urethral introduction. The working end of the shaft carries a liquid jet resection assembly that propagates first and second high-pressure liquid jet streams at vectors that intersect at a precisely controlled distance radially outward from the working end. The two liquid jet streams instantly cut tissue outward to the point of jet intersection or convergence. As the two high-pressure liquid jet steams converge within a selected range of angles, the jet stream undergoes a significant change in fluid velocity, resulting in a localized turbulence phenomenon, known as jet impingement. The turbulence leads to a dramatic reduction or even complete dissipation of kinetic energy capable of cutting tissue. This abrupt energy loss translates to a precisely defined cutting depth within the tissue. The calculated jet impingement thus results in a phenomenon that can be termed backstop turbulence and can be compared to the mechanical backstop shown in the high-pressure water jets of FIGS. 1A-1B. The system has a motor drive to adjust the spacing between the jet orifices in the working end, allowing the system to control the outward point of jet convergence and, consequently, the depth of tissue penetration, enabling highly controlled and predictable surgical cutting.

In an exemplary system variation, the convergence of the two high-pressure liquid jet streams occurs at angles ranging between 15° to 90°, and often between 30° to 60°, to control the backstop turbulence and energy dissipation zone. The kinetic energy dissipation within the turbulence occurs through several hydrodynamic interactions, including jet collision and partial mixing resulting in an immediate transfer of momentum. The kinetic energy of each jet stream is partially converted into pressure energy at the point of impact, where the water molecules from both jets mix and form turbulent regions. The jet streams'collision and resulting turbulence also dissipates kinetic energy through the creation of eddies of various scales, which can, in part convert the kinetic energy into heat via viscous dissipation. This aspect of energy loss is in part due to the friction within the fluids, causing a decrease in the macroscopic motion of water particles. The turbulence also dissipates energy relating to shear forces. The difference in velocity directions creates shear layers between the jets, leading to energy loss through viscous forces. These shear forces are particularly pronounced at the interfaces of the jets where they interact. Vortex formation also can form at the intersection point, further dissipating energy. These vortices can rotate at high speeds, converting the kinetic energy of the jets into rotational and then into thermal energy. The jet stream collision can also generate pressure waves, in the case of high-pressure jets. Such pressure waves can distribute energy throughout the fluid and towards tissue, reducing the kinetic energy of the jet streams impacting tissue.

The resection-cauterization device of the invention is further configured to deliver a vapor jet stream from the working of the device, which can cauterize or coagulate prostate tissue very rapidly. The cauterization component comprises a vapor generator device typically carried in a hub of the resecting-cauterization device. The vapor jet can deliver a water vapor that releases 540 cal/gram of energy from the vapor-to-liquid phase change to prostate before resection, during resection, or after resection. To cauterize surfaces of resected prostate tissue, calculations indicate that the total vapor jet delivery interval when delivering energy at 50 cal/sec to 100 cal/sec will be less than 120 seconds, and often less than 60 seconds. The total time interval for robotically resecting prostate with the dual jet liquid stream is expected to be less than 5 minutes, and often less than 4 minutes. Mapping the patient's prostate and resection profile using ultrasound and/or other imaging systems is expected to take 10 to 15 minutes. Thus, the entire procedure time using the present invention for volumetric reduction and cauterization in a BPH procedure is expected to be in the range of 20 to 25 minutes.

In another aspect of the invention, the automated resection can be assisted with artificial intelligence (AI) and/or machine learning wherein algorithms in the controller are adapted to monitor video imaging from the device's image sensor in real time to identify treatment site parameters and in response thereto can automatically modulate or terminate operation of the liquid jets, pressure of each jet stream, spacing of jet streams, operation of the vapor jet and cal/sec delivered, movement of the resecting assembly, operation of negative pressure source, or adjustment of the robotic arm.

The site parameters that the AI/machine learning algorithm monitors are, at least: image observable colors indicating bleeding, observable bubbles in images that indicate cavitation, observable collapse of side walls of the resection cavity, observable tissue debris that indicates sub-optimal cutting, color of tissue indicating cauterization or coagulation, tissue features indicating prostate tissue types, and identification of verumontanum, ducts and the like in the prostate.

DETAILED DESCRIPTION OF THE INVENTION

Figures 1A, 1B:
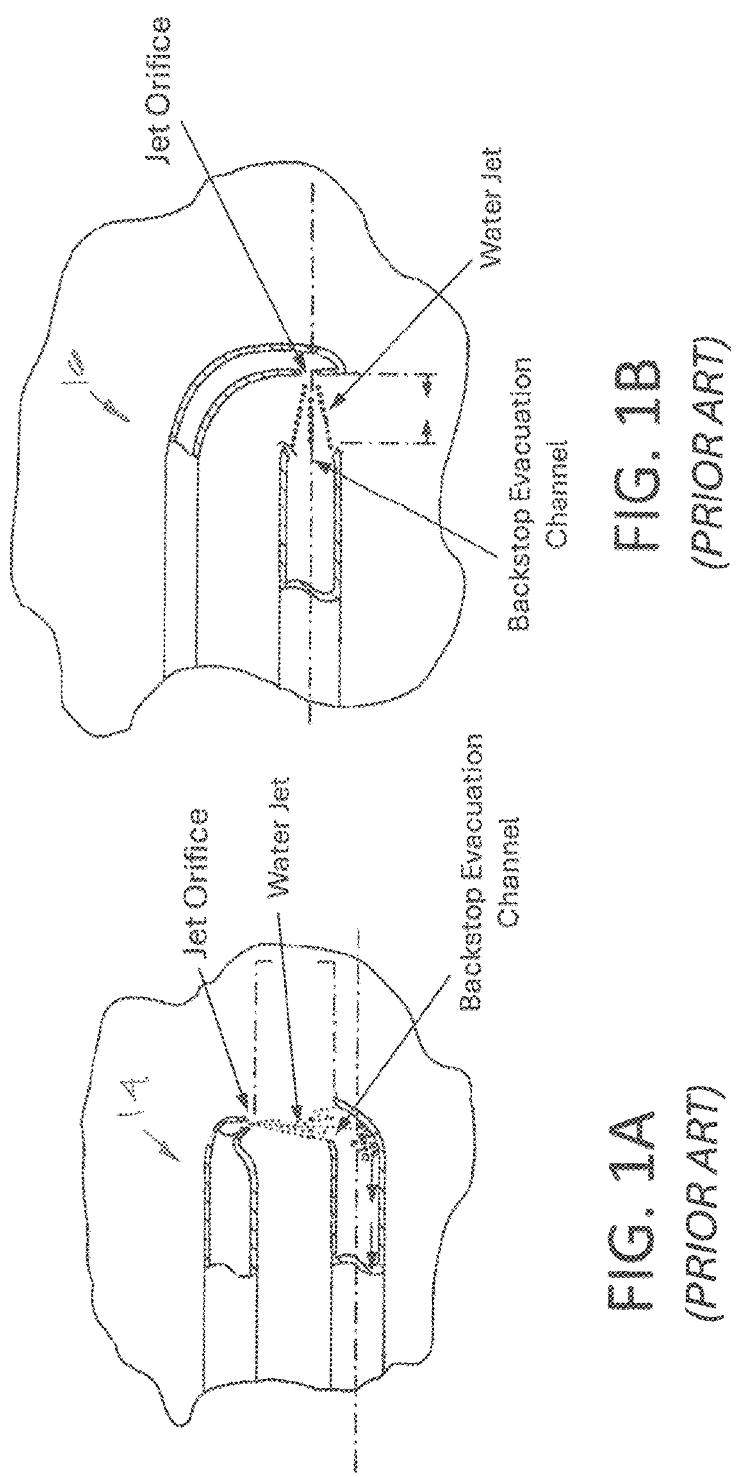
FIG. 1A is a prior art water jet resection device that directs a high-pressure water jet toward a backstop evacuation channel.
FIG. 1B is another prior art water jet resection device similar to that of FIG. 1A.
Figures 2A, 2B:
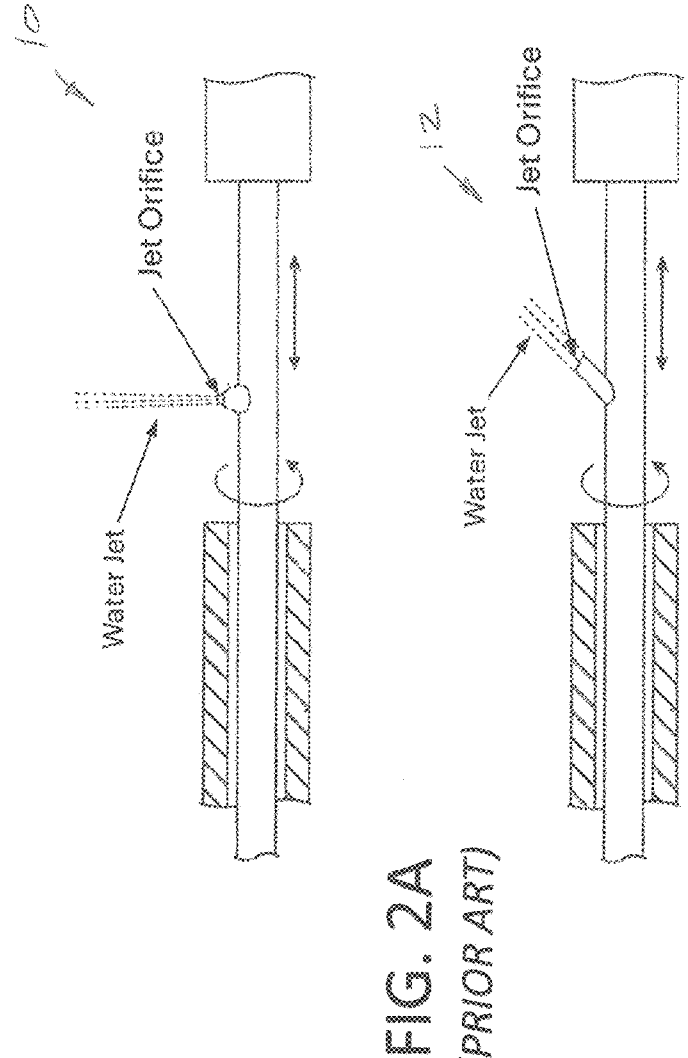
FIG. 2A is the working end of a prior art low-pressure water jet resection device that aims the water jet directly at tissue with no backstop.
FIG. 2B is a prior art water jet device similar to that of FIG. 2B.
Figure 3:
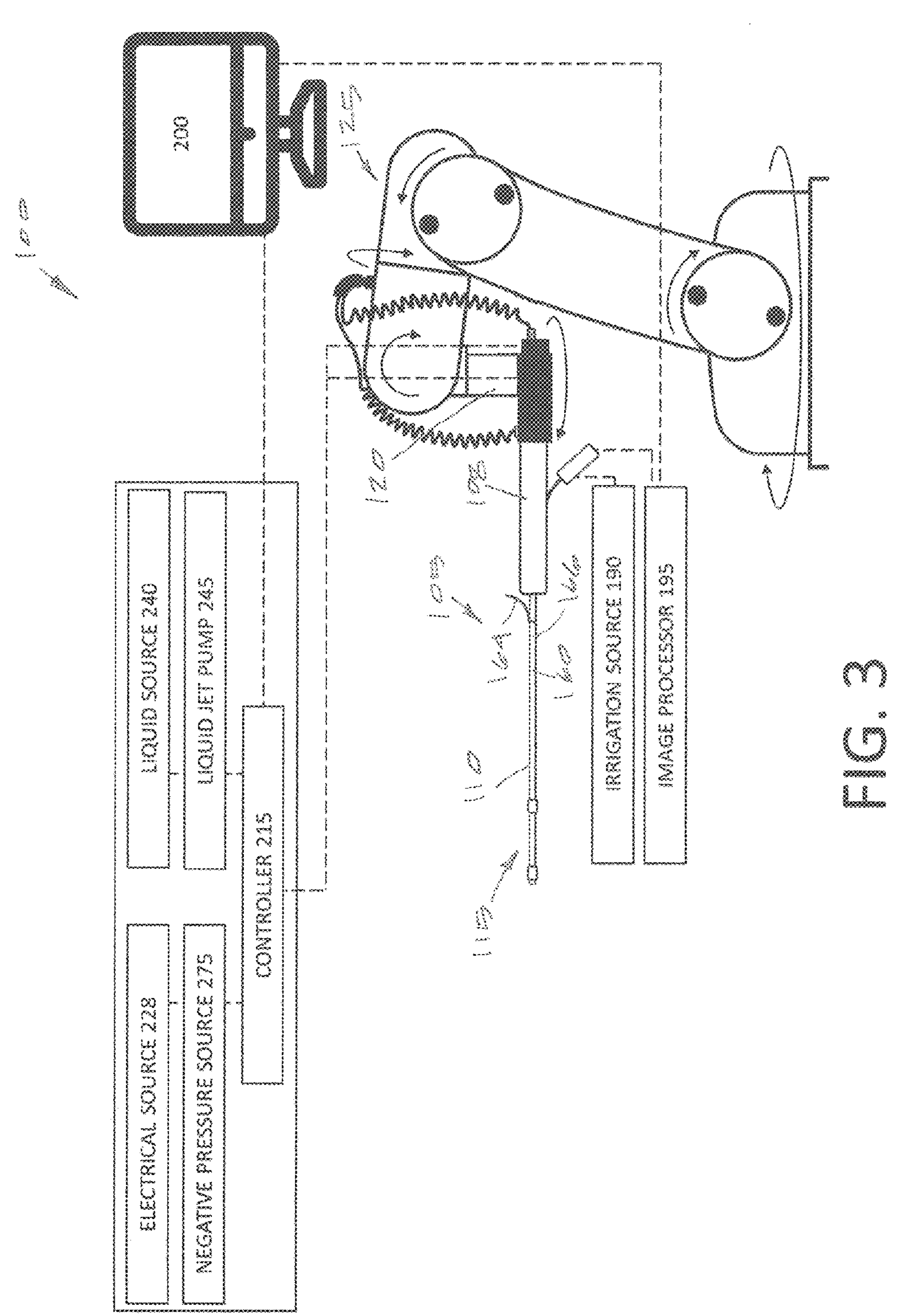
FIG. 3 is a schematic view of the resection authorization system the lock diagram of the components corresponding to the invention
Figures 4A, 4B:
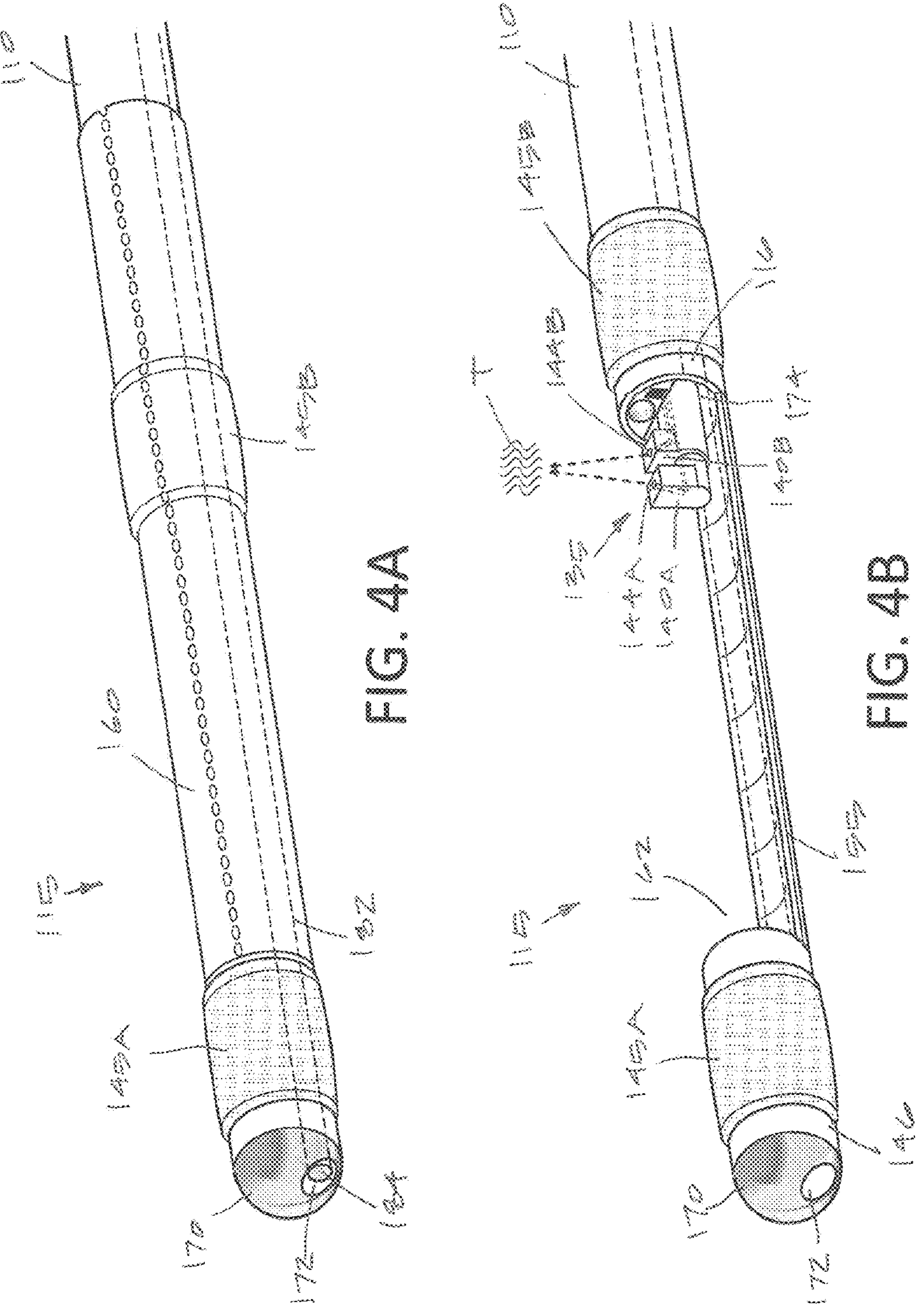
FIG. 4A is a perspective view of the working end the elongated shaft of the resection device of FIG. 3 with a tear-away sheath in place.
FIG. 4B is a view of the working end of FIG. 4A with the tear-away sheath removed.

FIGS. 3, 4A, and 4B illustrate a prostate treatment system 100 corresponding to the present invention and comprises a resection-cauterization device or probe 105 with a proximal handle or hub 108 coupled to an elongated shaft 110 extending about a longitudinal axis 112 to a working end 115 (FIG. 4A). The shaft 110 has a length suitable for transurethral introduction to a patient's prostate and bladder, and may have a length in the range from 15 cm to 25 cm. The diameter of the shaft 110 is in the range of 5 mm to 10 mm and typically is from 6 mm to 8 mm in diameter. The shaft 110 comprises an assembly of components further described below that are configured to provide high-pressure water jets at the working end 115 to resect prostate tissue to treat benign prostatic hyperplasia (BPH). The shaft 110 typically has an outer sleeve 116 of a thin-wall stainless steel or other metal (FIG. 4B) for providing column strength, but polymer extrusions also may be used.

As can be seen in FIG. 3, the resecting probe 105 is detachably coupled to a robotic arm 120 of a suitable robotic system 125 that provides multiple degrees of freedom of movement. In a method of use described below, the resecting probe 105 typically would be handled manually by the clinician to introduce the shaft 110 through the patient's urethra 126 to the prostate 128 and bladder 130 (see FIG. 5A). Thereafter, the clinician would couple the hub 108 of the resecting probe 105 to the robotic arm 120 which would then stabilize and lock the probe 105 and arm 120 in a suitable position. In a variation, the robotic system 125 has arms that can be moved freely by the clinician within several degrees of freedom to assume a selected position, and then the robotic system 125 can be actuated to lock the probe 105 into place. Thereafter, a controller described in detail below controls the robotic system 125 to manipulate the robot arms, motors, mechanisms, and drivers to operate the resecting probe 105.

Referring to FIGS. 3 and 4B, the working end 115 of the shaft 110 carries a resecting assembly 135 that comprises first and second water jet housings 140A and 140B having respective first and second jet orifices 144A and 144B that are described in detail below. The shaft 110 also carries first and second inflatable occlusion balloons 145A and 145B for anchoring the shaft 110 in the patient's urethra 126 as well as sealing the urethra from unwanted fluid escape during operation of the resecting assembly 135. The distal occlusion balloon 145A is positioned near the distal end 146 of the shaft 110 and communicates with a balloon inflation source 148 through an axial inflation channel in axial sidewall 155 of the outer sleeve 116 of shaft 110 (FIG. 4B). Similarly, the proximal occlusion balloon 145B communicates with an independent axial inflation channel in the shaft 110 communicating with the balloon inflation source 148. The balloon inflation source 148 for both balloons can consist of one or more manually operated syringes or a robotically operated pump mechanism.

Figure 5B:
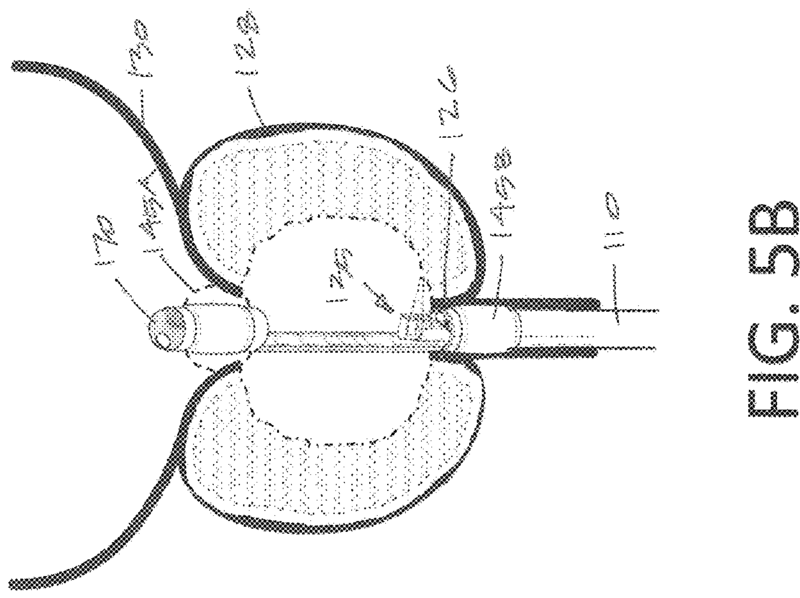
FIG. 5B is a view of the patient's prostate with the tear-away sheets removed from the working end after activation of the resection assembly to remove prostate tissue.
Figure 5A:
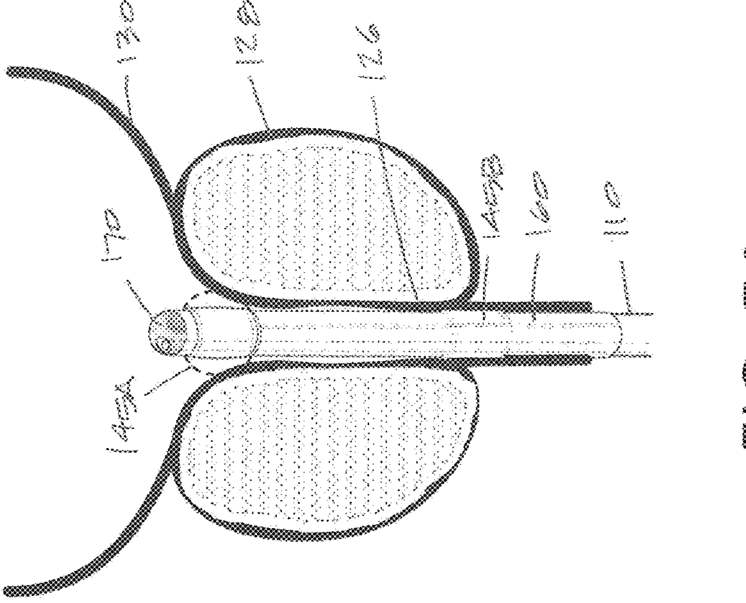
FIG. 5A is a sectional view of a patients prostate with the working end of the resection device of FIG. 3A introduced into the prosthetic urethra with the caraway sheet in place.

Referring to FIGS. 3 and 4A, it can be seen that the elongate shaft 110 is contained within a thin wall .tear-away sheath 160 that is configured to cover a sidewall cut-out 162 of the outer sleeve 116 of the shaft 110 that opposes the axial sidewall 155 (see FIG. 4B). The tear-away sheath 160 is a convenient way to provide a very thin wall element to assist in advancing the working end 115 and shaft 110 through the patient's urethra 126 to the prostate 128 and bladder 130 (FIG. 5A). FIG. 4B shows the first and second water jet housings 140A and 140B are configured to move helically within the sidewall cut-out 162. In another variation, a retractable metal sleeve can be provided to cover the sidewall cut-out 162. However, the tear-away sheath 160 of FIGS. 3 and 4A have the advantage of being thinner and can be shaped to extend over the proximal occlusion balloon 145B. As can be seen in FIG. 3, a pull tab 164 is provided on the proximal end 166 of the tear-away sheath 160 for manually pulling and extracting the sheath 160 from the patient.

FIG. 5A illustrates the working end 115 of the shaft 110 after being introduced through the urethra 126 into the prostate 128. In FIG. 5A, the tear-away sheath 160 is still in place. FIG. 5B shows the working end again in the patient's prostate 128 after the tear-away sheath 160 has been removed.

Figure 6:
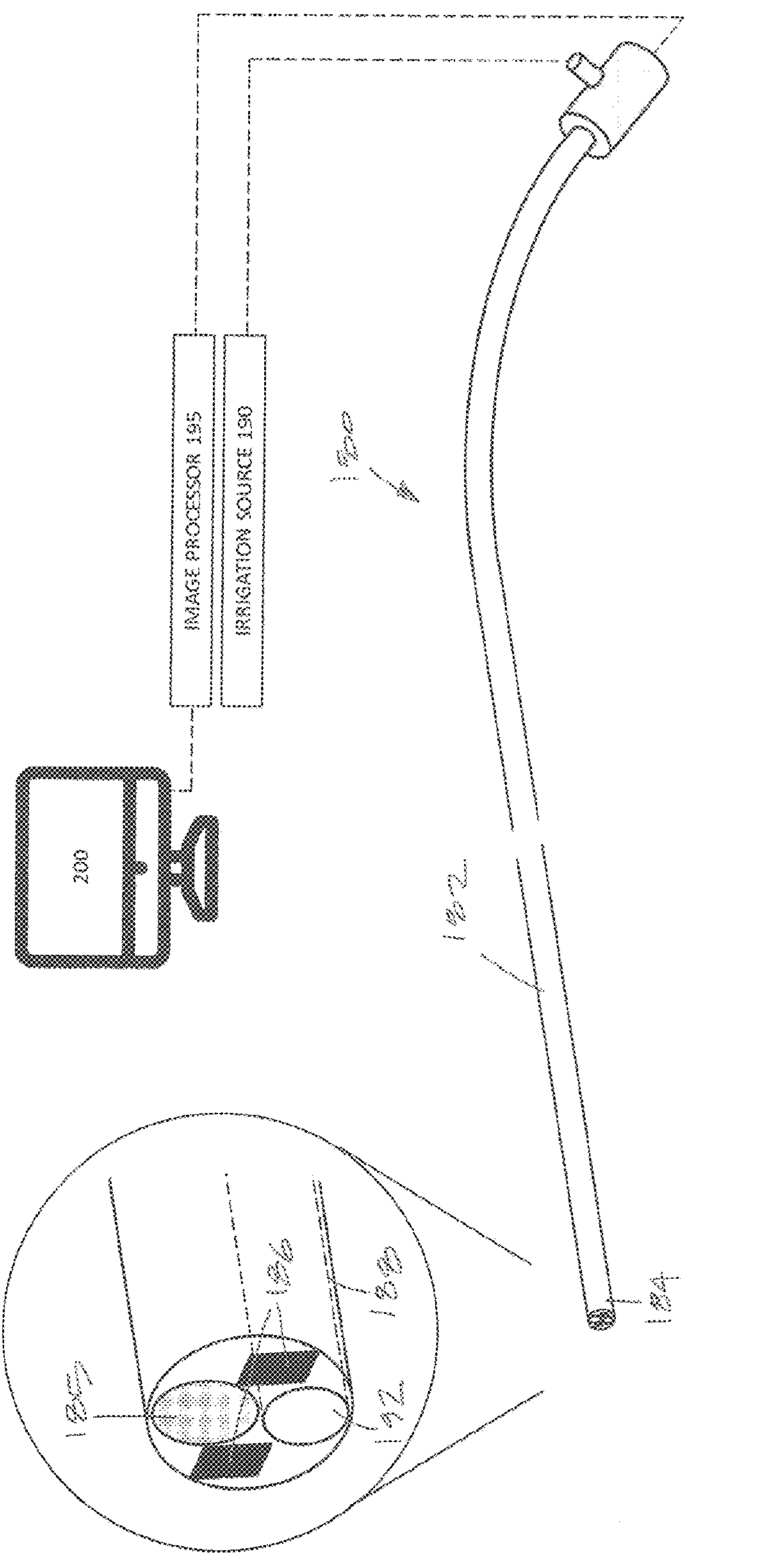
FIG. 6 illustrates an endoscope that's configured for insertion and removal from the shaft of the resection device.

In FIG. 4A, it can be seen that the blunt distal tip 170 of the shaft 110 has a port 172 therein that comprises the open termination of an elongate passageway 174 (FIG. 4B) extending through the shaft 110 that is configured to receive an endoscope. It can be understood that for introduction of the shaft 110 through the patient's urethra 126, the clinician would be aided by endoscopic viewing and irrigation with saline or another liquid or gel. In a variation, an endoscope 180, as shown in FIG. 6, is insertable and removable from the passageway 174 in shaft 110. The endoscope 180 as shown in FIG. 6, comprises an elongate endoscope shaft 182 with a distal end 184 carrying an image sensor 185 and at least one LED with two LEDs 186 shown in FIG. 6. The endoscope shaft 182 further carries an irrigation channel 188 communicating with a remote fluid irrigation source 190 to provide a fluid flow outward from the open end 192 of the irrigation channel 188. The endoscope shaft 182 has a diameter ranging from 2 mm to 5 mm and can be rigid or flexible. As shown in FIGS. 6 and 8, a flexible endoscope shaft 182 allows for introduction of the endoscope 180 through a curved channel 194 in the hub 108 that transitions into the passageway 174 in the elongate shaft 110 of the resecting probe 105. In a variation, the image sensor is an Omni Vision model OCHFA10 sensor module that integrates the image sensor, a processor, and lenses in a miniature wafer-level module. The endoscope 180 can be configured as a single-use component or a multiple-use component. In another variation, the hub 108 of FIG. 7 and the motor drive mechanisms therein can be designed with a straight passageway extending from the hub 108 to the distal tip 170 of the shaft 110 to then allow use of a straight, rigid shaft endoscope 180. As can seen in the block diagram of FIG. 6, the image sensor 185 of the endoscope 180 is coupled to an image processor 195 and display 200 for viewing images from the endoscope 180. The irrigation source 190 can be a gravity system or any suitable positive pressure pump system known in the art.

Figure 7A:
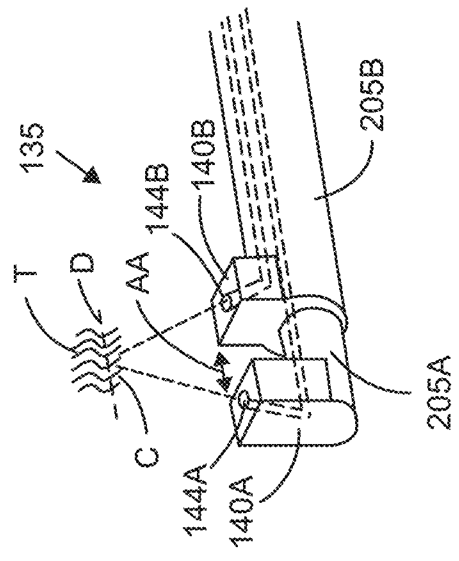
FIG. 7A illustrates the resection assembly comprising first and second liquid jet streams in a first position configured for a shallow cutting depth.
Figure 7B:
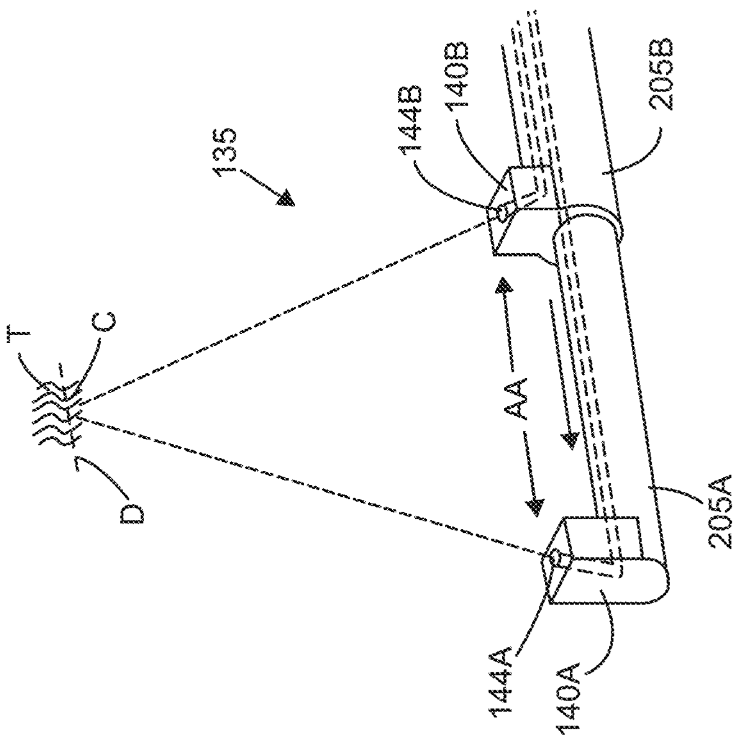
FIG. 7B illustrates the resection assembly of FIG. 7A with the first liquid jet stream and the second liquid jet stream in a second position configured for deeper cutting depths.
Figure 8:
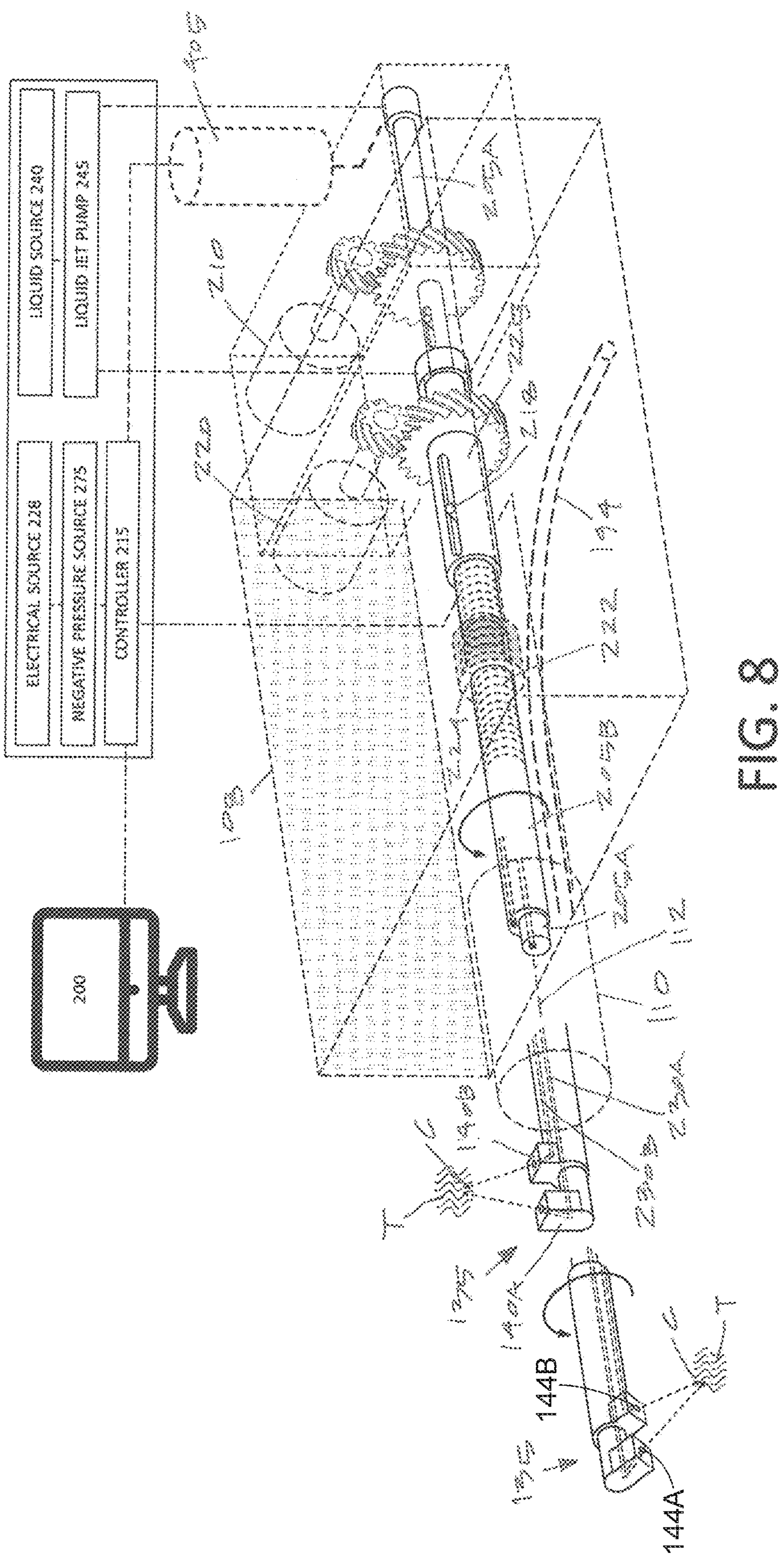
FIG. 8 is a schematic view and block diagram of components of the resection-cauterization system.

Now, turning to FIGS. 4B, 7A, 7B, and 8, the water jet resecting assembly 135 can be described in detail. FIG. 4B illustrates the first and second water jet housings 140A and 140B and respective first and second jet orifices 144A and 144B exposed in the cut-away sidewall 162 of the probe shaft 110. FIGS. 7A and 7B are enlarged views of the jet resecting assembly 135. In a variation, the first jet orifice 144A is carried in the first jet housing 140A comprising the distal end of a first inner water jet sleeve 205A extending through the shaft 110. The second jet orifice 144B is carried in the second jet housing 140B comprising the distal end of a co-axial second water jet sleeve 205B that is axially moveable over the first sleeve 205A. A first motor drive 210 (FIG. 8) is operated by a controller 215 coupled to either the first sleeve 205A to adjust the axial spacing AA between the two jet orifices 144A, 144B.

Referring to FIG. 8, the first and second water jet sleeves 205A, 205B are coupled with a spline 218 to maintain the jet orifices 144A, 144B at the same radial angle relative to the shaft axis 112. A second motor drive 220 is controlled by the controller 215 to move the dual jet resecting assembly 135 helically at a very fine pitch. FIG. 8 shows that a proximal end 222 of the outer jetting sleeve 205B is configured with a lead screw element 224 so that the second motor drive 220 rotates a drive sleeve 225 which in turn is splined to the outer jetting sleeve 205B to actuate the sleeve assembly and resecting assembly 135 helically. Thus, it can be understood that the first and second motor drives 210, 220 are connected to electrical source 228 and operated by the controller 215 to move the jet resecting assembly 135 helically in an axial direction contemporaneous with the first motor drive 210, adjusting the spacing between the dual intersecting jets exiting the jet orifices 144A, 144B. The motor drives 210, 220 comprise stepper motors that are controlled by the controller 215 to control the radial angle of the jet orifices 144A, 144B and the spacing between the jet orifices to thereby cause the liquid jet streams to resect and obliterate tissue radially outward from the shaft axis 112 at various selected depths and radial angles. This system allows for resection of any shaped space both axially and radially outward from the shaft axis.

As can understood from FIGS. 7A and 7B, the spacing AA between the first and second jet orifices 144A, 144B is designed to adjust the radially outward point of jet intersection or jet convergence C. The converging jets at point C, in effect, result in a "backstop" where the kinetic energy of both jets is dissipated, which thus allows for accurate control of the radial outward cutting depth. As the two high-pressure water jets converge and intersect, the flow of jets becomes highly turbulent. This localized turbulence phenomenon, also called jet impingement, leads to a tremendous reduction or substantially complete dissipation of the level of kinetic energy within the liquid jet streams that would be capable of cutting tissue. This abrupt energy loss translates to a defined cutting depth D outward from the jetting orifices 144A, 144B (FIGS. 7A-7B). By adjusting the spacing AA between the jet orifices 144A, 144B in the working end 115, the clinician can precisely control the point of jet convergence C and, consequently, the depth of tissue penetration, thus enabling highly controlled and predictable resection.

In an exemplary system variation, the intersection and subsequent interaction of the two high-pressure water jets is configured to occur at angles ranging between 15° to 90° degrees to provide a controlled energy dissipation zone that can terminate tissue obliteration. The kinetic energy dissipation occurs through several hydrodynamic interactions. In a first aspect, the intersecting jets result in jet collision, partial mixing and turbulence. When the first and second jets collide at an angle in the range described above, there is an immediate transfer of momentum. Each jet's kinetic energy is partially converted into pressure energy at the point of impact, where the water molecules from both jets mix and form turbulent regions.

The angle between the two jets influences the nature of this interaction. At lesser angles, for example, 15° to 20°, the jets can tend to merge to some extent without excessive turbulence, which can result in less immediate energy dissipation compared to greater angles of intersection. At higher angles, for example, 30° to 45°, the interaction is abrupt, leading to a higher energy dissipation rate due to increased turbulence. Thus, the collision and partial mixing of the two jet streams results in turbulence that dissipates kinetic energy through the creation of eddies of various scales, which can, in part, convert the kinetic energy into heat via viscous dissipation. This aspect of energy loss is in part due to the friction within the fluids, causing a decrease in the macroscopic motion of water particles.

Another energy dissipation mechanism relates to shear forces. The difference in velocity directions creates shear layers between the jets, leading to energy loss through viscous forces. These shear forces are particularly pronounced at the interfaces of the jets where they interact. Vortex formation also can form at the intersection point, further dissipating energy. These vortices can rotate at high speeds, converting the kinetic energy of the jets into rotational and then into thermal energy.

The jet collision can also generate pressure waves, in the case of high-pressure jets. Such pressure waves can distribute energy throughout the fluid and towards tissue, reducing the kinetic energy of the jet streams impacting tissue. If the pressure at the point of jet intersection drops sufficiently, cavitation may occur, where the liquid vaporizes into small voids or bubbles. The collapse of such cavitation bubbles can further cause energy dissipation through acoustic energy and micro-jetting, which, in turn, can lead to further energy loss through friction and heat.

Figures 9A, 9B:
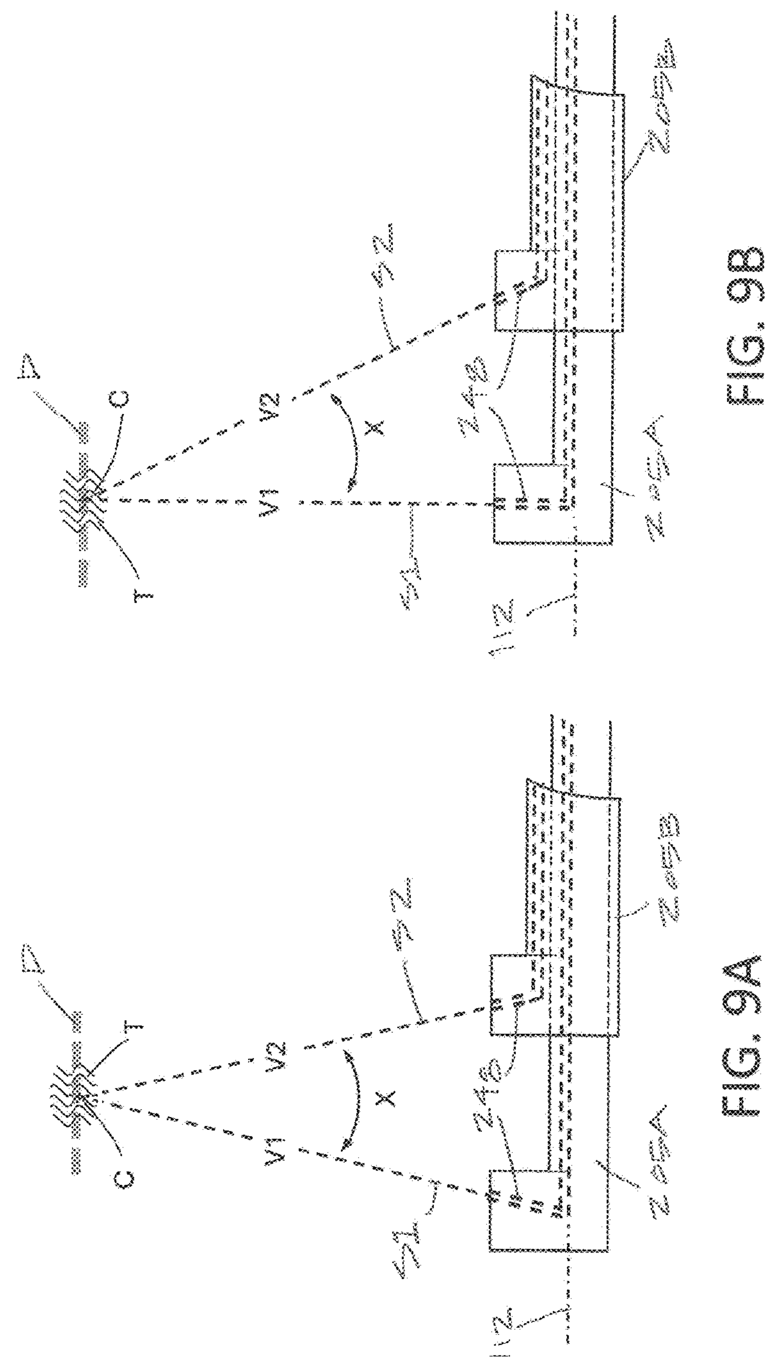
FIG. 9A is an elevational view of a variation of the first and second resecting sleeves illustrating the angle of propagation vectors of the dual liquid jet streams.
FIG. 9B is an elevational view of a variation similar to that of FIG. 9A wherein the dual jet streams have propagation vectors with different angles.

Referring to FIGS. 8 and 9A, the inner jetting sleeve 205A has a fluid channel 230A extending through the sleeve that communicates with a liquid source 240 and liquid jet pump 242 (FIG. 8). The outer jetting sleeve 205B has a fluid channel 230B extending through the sleeve that communicates with the liquid source 240 and a liquid jet pump 245, wherein either a single jet pump can be used to provide flows to both jet streams or typically independent jet pumps are be used to allow the controller 215 to adjust pressure between the jet streams (FIG. 8).

In FIG. 9A, it can be seen that the first and second jet streams S1 and S2 are angled similarly but converging relative to the axis 112 of the sleeves and shaft 110 (FIG. 7A). In FIG. 9A, the angle of intersection X of the vectors V1 and V2 of the jet streams S1, S2 is important for causing the desired backstop turbulence T and is between 15° and 90° and often between 20° and 45°. FIG. 9B illustrates a variation wherein the jet stream vectors V1, V2 differ relative to the axis 112 of the sleeve assembly, but the range of the angle of intersection X remains similar. The angle of the jet stream vectors V1, V2 relative to the axis 112 range from 45° to 90°.

FIGS. 9A and 9B also depict a linear alignment channel 248 inward from each jet orifice 140A, 140B that is adapted to align the fluid flow with the jet orifice and vector V1, V2 wherein the length of the channel 248 is at least 0.5 mm or at least 1.0 mm.

Figure 10:
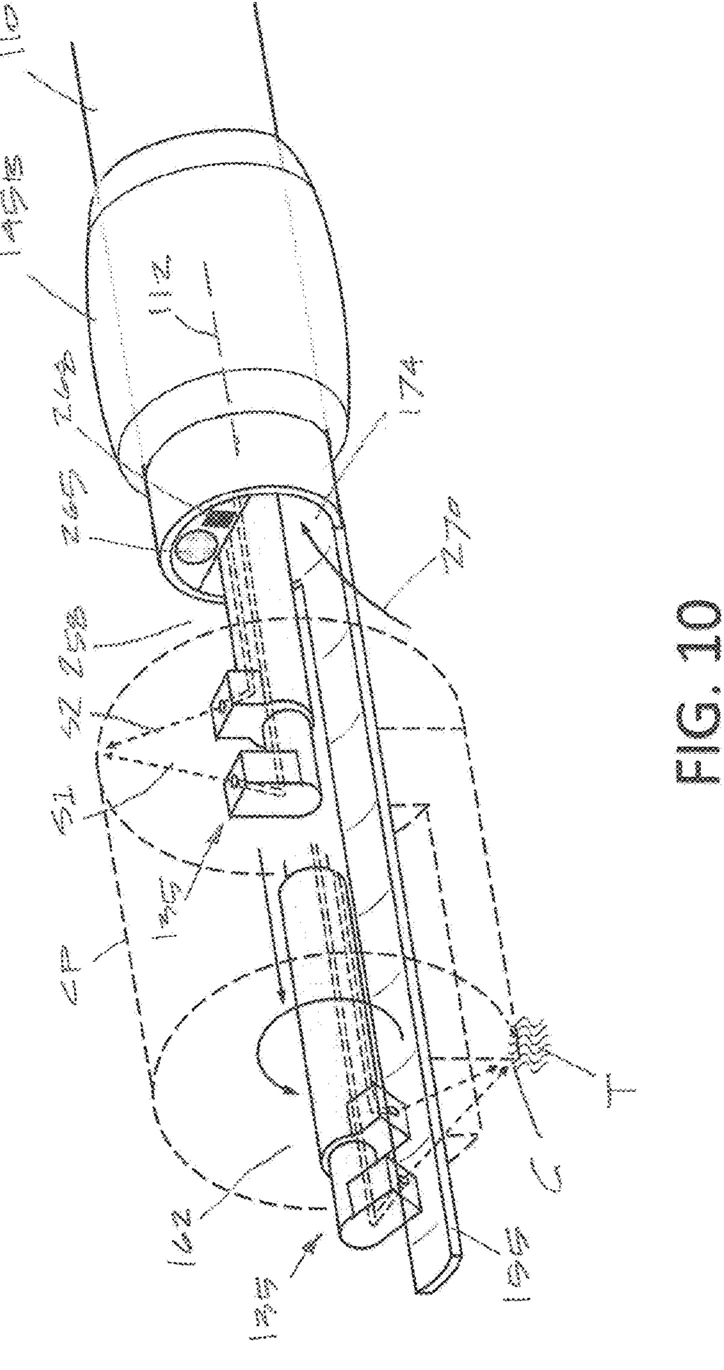
FIG. 10 is a schematic view a cylindrical resection profile of tissue removed with the resecting assembly of the invention.

FIG. 10 illustrates the jet resection assembly helically advanced around axis 112 to cause the sweeping motion to resect a cylindrical path CP in prostate tissue. The use of a helical lead screw for advancing and retracting the jet assembly is advantageous as only a single stepper motor 220 is required (FIG. 8). In FIG. 10, it can be understood that the controller 215 is adapted to monitor the angle of rotation of the jet assembly 135 from a set point, and the controller 215 de-activates the liquid jet streams S1, S2 as the helical rotation approaches the axial sidewall 155 end re-activates the jet streams S1, S2 as a helical movement angularly advances past the sidewall 155. In another variation, helical actuation of the resecting assembly 135 can be replaced with a different mechanism that comprises a first stepper motor to provide axial translation of the assembly and a second stepper motor to provide rotation of the jet assembly, which can produce similar resection results.

Still referring to FIG. 10, it can be seen that the proximal end 258 of the sidewall cut-out 162 carries an image sensor 265 and at least one LED 268 for viewing the targeted tissue being resected by the liquid jet streams. In FIG. 10, the resected tissue debris and fluid are extracted as indicated by arrow 270 through the open passageway 174 in the introducer sleeve. This passageway is coupled to negative pressure source 275 (FIG. 8). Passageway 174 is the same passageway that carried the removable endoscope 180 of FIG. 6 that was used during a first step of the procedure.

Figure 11A:
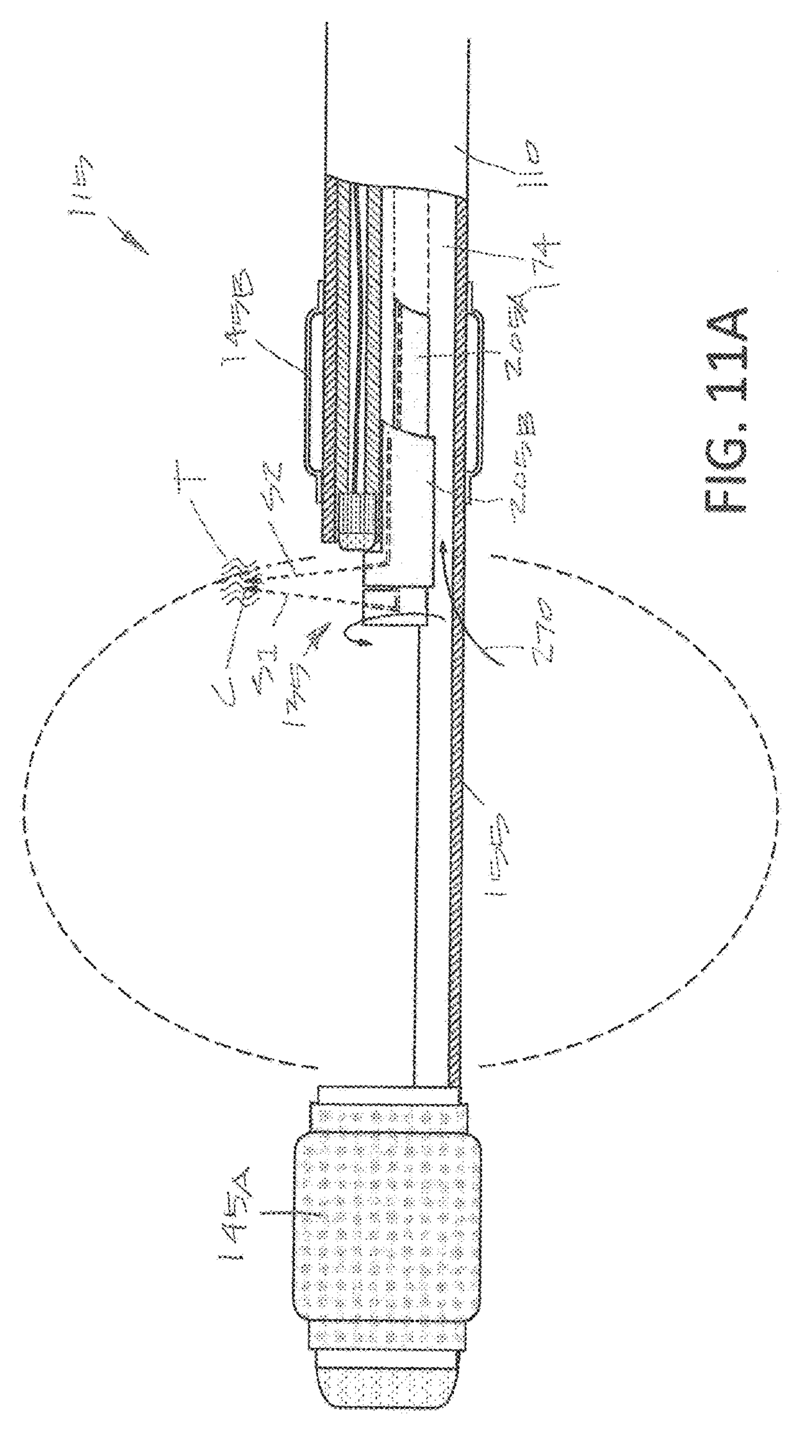
FIG. 11A is a cut-away elevation view of a step in a method of operating the resection assembly to resect a non-cylindrical volume of tissue commencing with a shallow cutting depth.
Figure 11B:
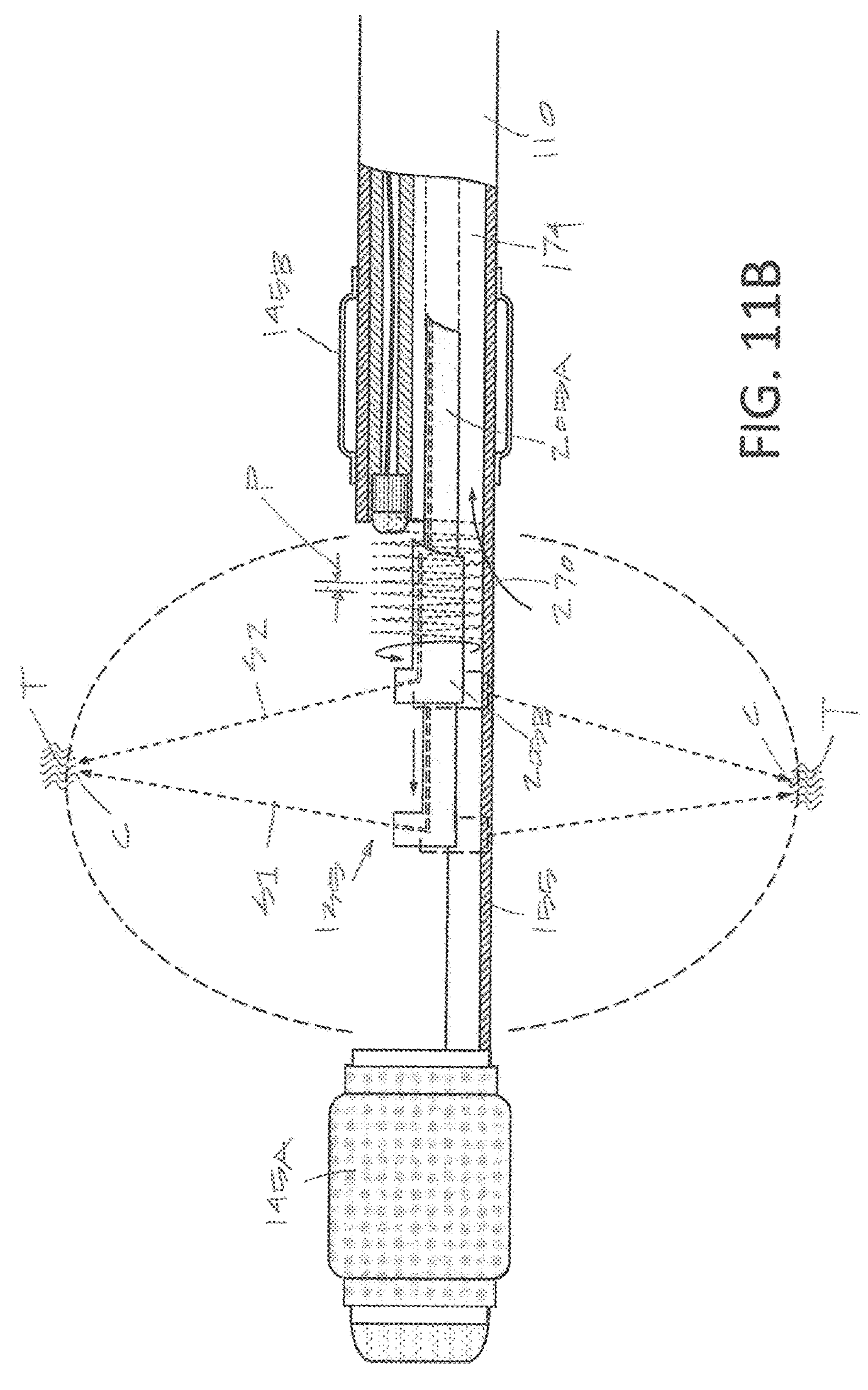
FIG. 11B is a subsequent step wherein the robotic controller adjusts the dual liquid jet streams to provide a deeper cutting depth while advancing the resection assembly helically.
Figure 11C:
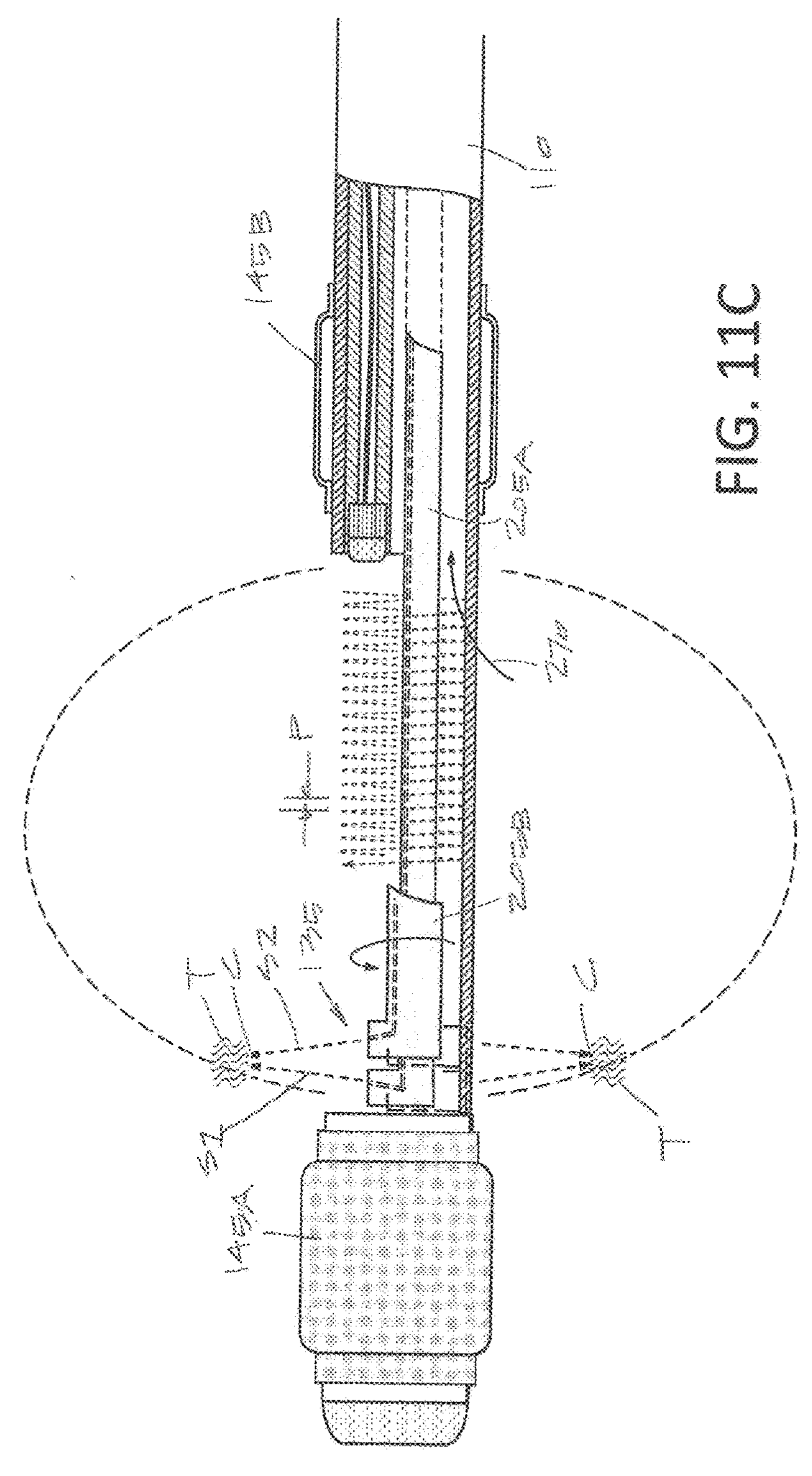
FIG. 11C is another subsequent step wherein the robotic controller adjusts the dual liquid jet streams to provide a shallow cutting depth while advancing the resection assembly helically.

Now, turning to FIGS. 11A-11C, a cut-away elevational view of the working end 115 shows a sequence of how the jet resecting assembly 135 when stabilized in place in the prostatic urethra, can resect any selected profile of prostate tissue outward from the prostatic urethra. In FIG. 11A, it can be seen that the first and second jet streams S1 and S2 are spaced close together and the jet streams intersect at convergence point C close to the shaft 110. FIG. 11B shows the first and second jet streams S1, S2 spaced apart by the first motor drive 210 (FIG. 8) while at the same time second motor drive 220 has helically advanced the jet assembly 135 in the distal direction, thereby cutting to a greater depth. FIGS. 11A-11C show that the pitch P of helical movement is very small so that each 360° helical movement is very close to the previous 360° helical movement to remove tissue in a continuously overlapping cutting path. The pitch, defined as axial advancement in 360° can be from 0.5 mm to 2.0 mm. FIG. 11C shows the jet resecting assembly 135 advanced further distally in the sidewall cut-out 162 wherein the motor drive 210 has moved the first and second jet orifices 144A, 144B closer together to reduce the cutting depth. Thus, it can be understood from FIGS. 11A-11C that any depth profile and resection contour can be achieved with the dual jet resecting assembly 135.

Figure 12:
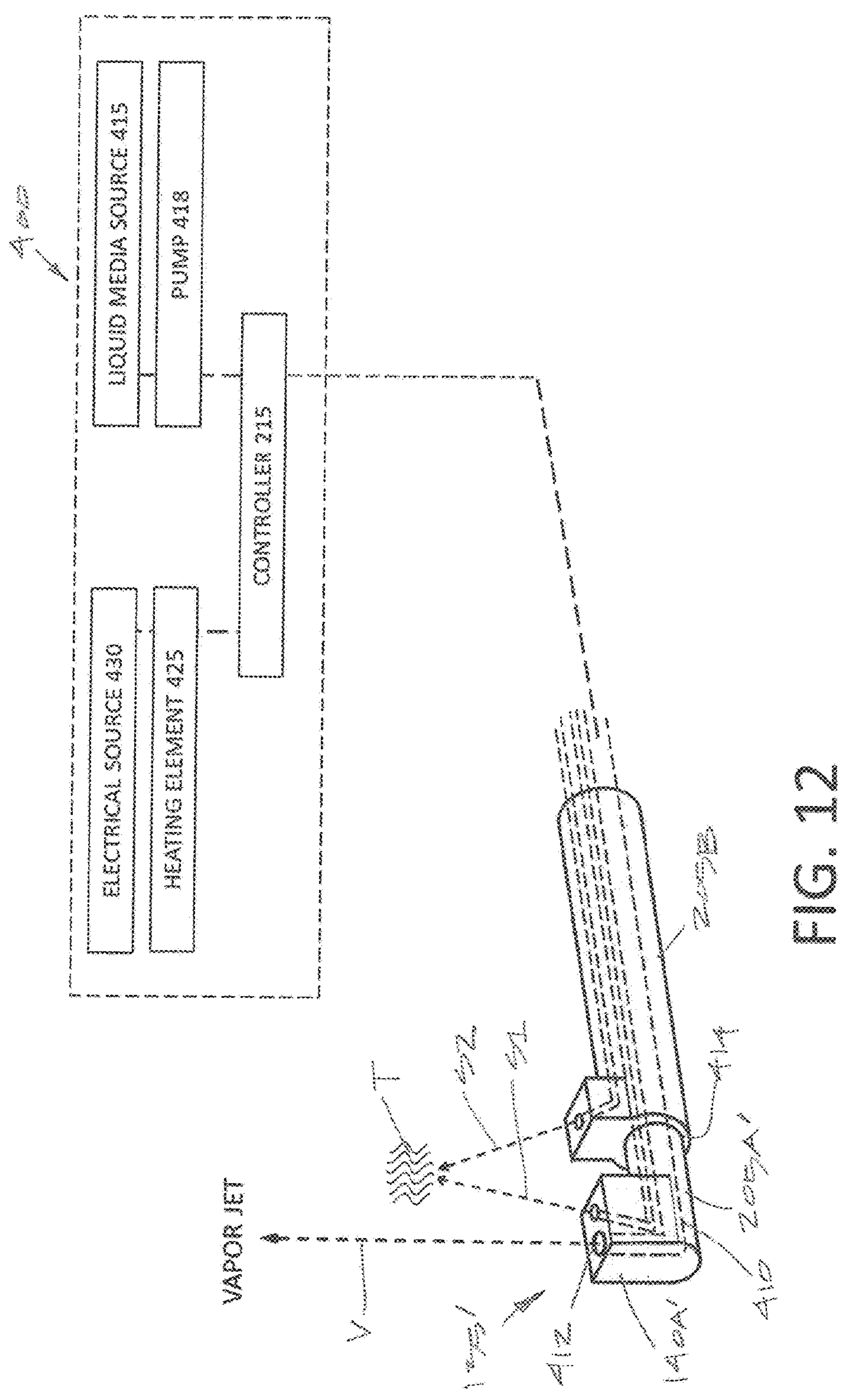
FIG. 12 is a block diagram of the vapor generator system adapted for delivering a vapor jet stream from the working end to cauterize tissue.
Figure 13:
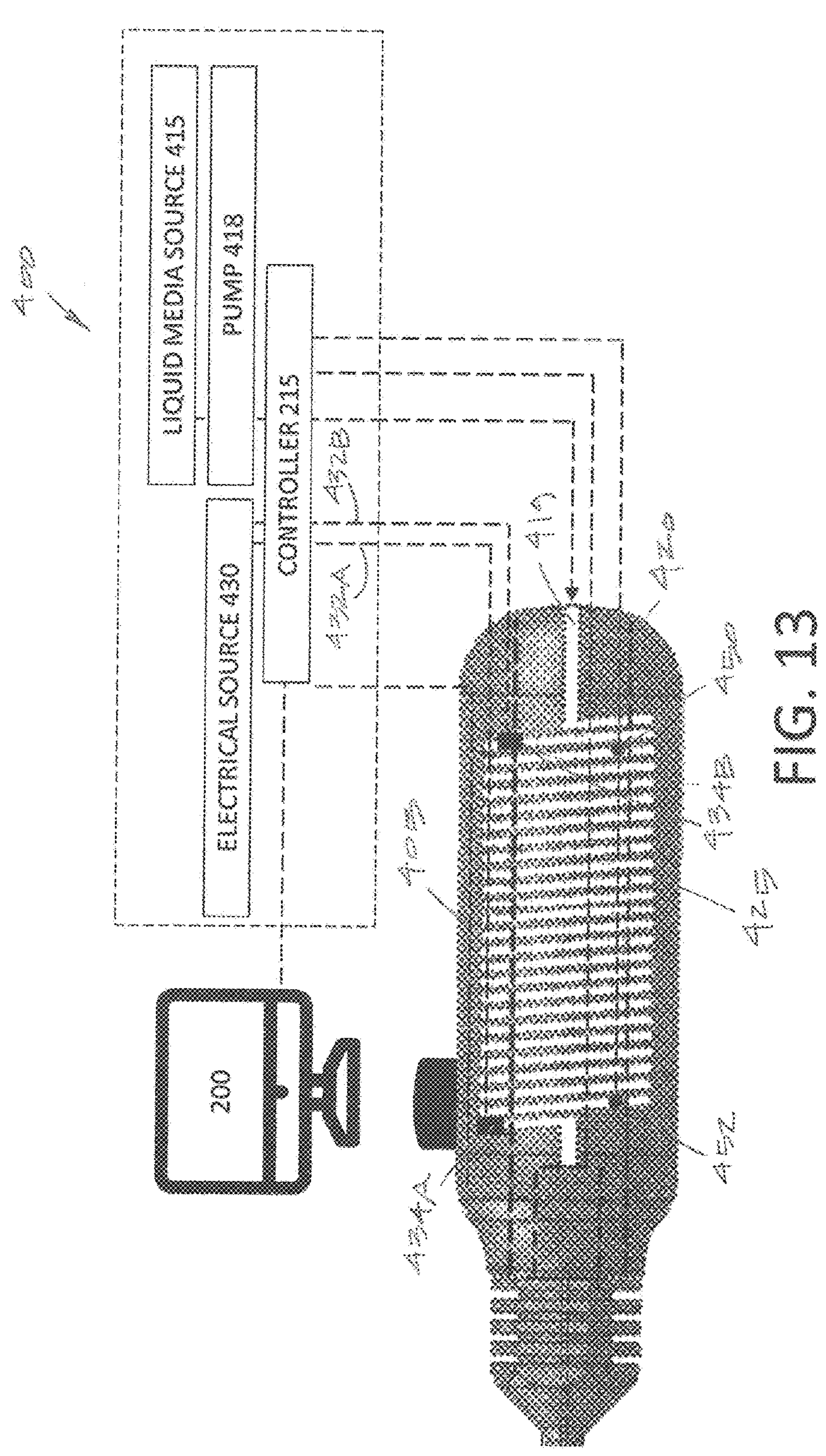
FIG. 13 is a view of components of the vapor generator system within a housing.
Figure 14B:
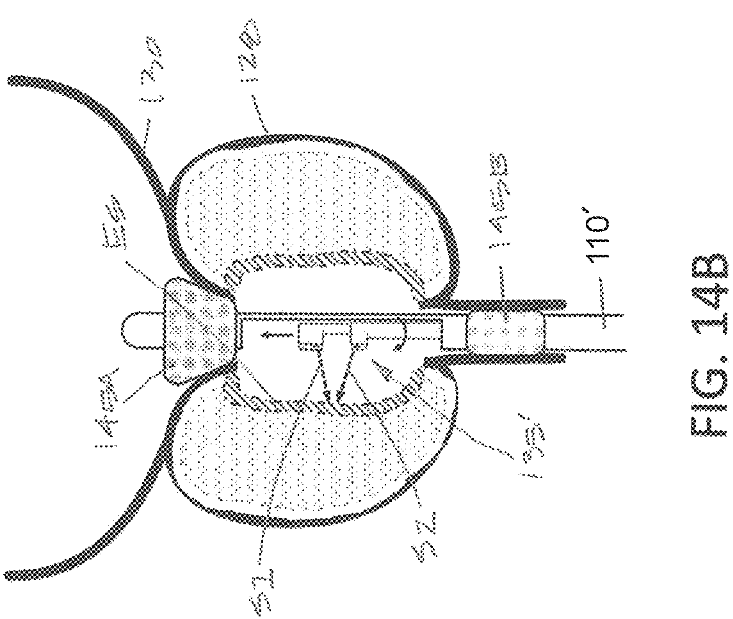
FIG. 14B is a subsequent step wherein the vapor jet is terminated, and thereafter, the dual liquid jet assembly is actuated to resect tissue in the coagulated zone.
Figure 14A:
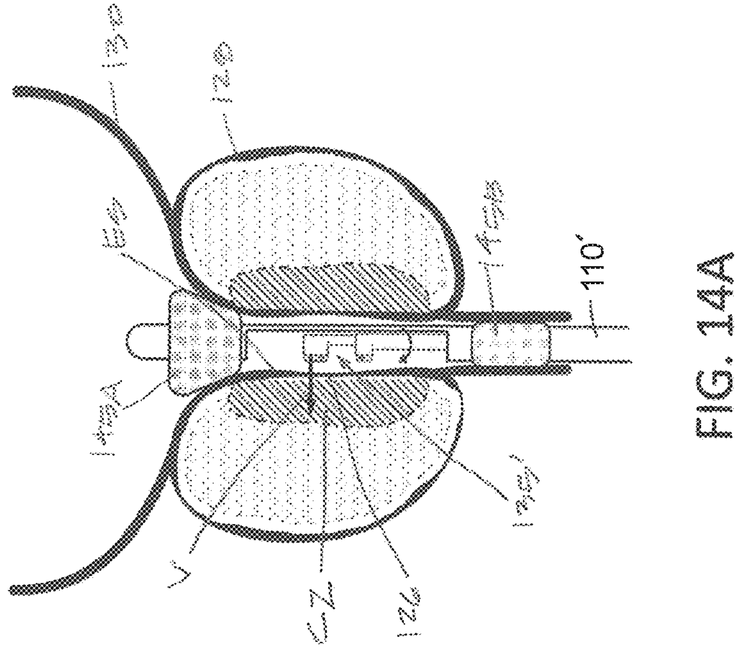
FIG. 14A is a sectional view of an initial step in a method of the invention wherein the vapor delivery system is actuated to provide a vapor jet stream to coagulate a tissue zone around the prostatic urethra that is targeted for resection.

FIGS. 12 and 13 illustrate the cauterization system 400 that is added to a resection assembly 135' similar to that of FIGS. 3 to 8. In a variation, the cauterization system 400 comprises a vapor generator device 405 (FIG. 13) that typically is carried in the hub 108 of the resecting device 105 (FIG. 3) or is attachable thereto. FIG. 8 schematically shows the vapor generator device 405 coupled to the hub 108, and, more specifically, to sleeve 205A. In a variation, the vapor delivery device or handle 405 is adapted to deliver a high-energy thermal water vapor or similar vapor to a treatment site in the patient's prostate to cauterize tissue. The delivery of a water vapor site can deliver 540 cal/gram of water energy to the exposed surfaces ES of the resected cavity, which can instantly cauterize the exposed surface ES (FIGS. 14A-14B). In the variation of FIG. 12, the resecting assembly 135' is the same as described previously, except that the inner jetting sleeve 205A' has a vapor inflow channel 410 therein extending to the distal housing 140A' and vapor jet outlet 412 from which a vapor jet stream V is propagated outward. It should be appreciated that the vapor jet stream V can cauterize the targeted exposed surface of tissue no matter the location of the vapor outlet 412 in the resecting assembly 135' or the working end. For example, the vapor flow channel 410 and vapor outlet 412 can be in the inner sleeve 205A' as shown in FIG. 12, the outer sleeve 205B, in the annular space 414 between the inner and outer sleeves 205A' and 205B, in the outer sleeve 116 or the axially extending member 155 (FIG. 10).

FIG. 13 illustrates the components of the vapor deliver system 400 with a fluid media source 415 positioned remote from the vapor generating handle 405 with pump 418 comprising a syringe pump actuated by stepper motor (not shown) to pump a fluid media from the liquid media source 415 into a flow channel 419 extending through tube 420 that is partly formed into a helical heating element 425. In a variation, the heating element 425 is a metal that can be resistively heated and can be coiled, straight, or a combination thereof to a suitable shape for disposing in handle 405. In FIG. 13, the heating element 425 comprises the helical portion of tube 420 to provide a compact form factor for disposing in the handle 405. In a variation, a direct current (DC) electrical source 430 or power supply generates a DC current that is coupled to the heating element 425. In other variations, the DC current can be supplied from a battery, for example, a 12 Volt or 24 Volt DC power supply. FIG. 13 illustrates electrical leads 432A and 432B are connected to the heating element 425 at connections 434A and 434B, respectively, on opposing ends of the helical-formed heating element 425.

As can be understood from FIG. 13, the controller 215 also can control pump 418, which is configured to pump the liquid media from the liquid media source 415 into and through the tubing 420 to the heating element 425 to generate the water vapor stream V. In operation, the controller 215 is adapted to precisely control the flow rate of liquid media and the temperature of the resistively heated heating element 425 to convert the liquid media into a vapor media in the helical tubing to thereby provide a high-quality vapor stream V exiting the vapor outlet 412 as shown in FIG. 12.

In the variation of FIG. 13, the display 200 is also coupled to the vapor generating system 400, which can be a touch-screen display for selecting operating parameters of the system, displaying alerts, and providing other operating information. The system 400 thus comprises a flow-based vapor delivery system, and typically, the pump 418 and stepper motor are operated by the controller 215 and allow for very precise control of flow rates of liquid media into the helical heating element 425. In a variation, the interior flow channel of the helical heating element 425 has a diameter between 0.02" and 0.10" and a flow channel length of between 20 cm and 200 cm. The outside diameter of the helical heating element 425 as an assembly can be from 5 mm to 20 mm. In a variation, the helical heating element 425 can be formed of a stainless steel, Inconel, or any other suitable resistively heatable metal.

In a typical variation, the helical heating element 425 carries at least one temperature sensor coupled to the controller 215 and is shown in FIG. 13 with two temperature sensors 450 and 452 at proximal and distal ends of the helical heating element 425. In another variation, a third temperature sensor (not shown) is carried in a medial portion of the helical heating element 425. The plurality of temperature sensors is adapted to send temperature signals to the controller 215, and thereafter, the controller algorithms, in response to the temperature signals, modulate operation of the pump 418 and its flow rate and/or the energy delivered from electrical source 430 to insure the generation of high-quality vapor stream V is provided within the heating element 425 which then results in the desired cal/sec delivered from the vapor delivery outlet 412 (FIG. 12).

It can be understood that the design parameters of the pump 418 and fluid inflow rates, the heating element 425, and the electrical source 430 are inter-related, and in general, a typical system is designed to provide a selected calories/second rate of applying energy to tissue that is optimal for the tissue cauterization procedure. In general, the inter-related design parameters include (i) ml/min of liquid media flow within the helical heating element 425, which further is dependent on flow channel diameter, flow channel length, and flow pressure; (ii) the power delivered by the electrical source 430 which further relates to helical tubing design and materials, and ultimately results in a selected vapor quality, i.e., the percent of the flow exiting vapor jet outlet 412 that is phase changed to pure vapor as opposed to non-phase changed liquid droplets. In a variation, system provides a flow of vapor that is greater than 90% pure vapor and further provides an ultimate conversion efficiency of electrical energy to vapor energy of at least 60%.

In a variation, the controller 215 operates the electrical source 430 to deliver at least 100 W, together with delivering sterile water as a liquid media with pump 418 at a flow rate of between 1 ml/min and 5 ml/min into the helical heating element 425 having a flow channel with a diameter of 0.05" and a length 50 cm with the helical tubing portion having a diameter of 10 mm. In another variation, the controller 215 can be configured to monitor voltage across the heating element 425, and the current through the heating element 425 can be determined to provide an accurate, real-time measurement of power being dissipated into the fluid flow and the heating element 425.

FIGS. 14A to 14D illustrate the steps of a method corresponding to the invention using the resecting assembly 135' and vapor delivery system 400 to cauterize tissue during a resection procedure. In general, the vapor delivery system 400 can be used in one of several ways to cauterize tissue in a BPH resection procedure. For example, system 400 can provide a vapor jet stream V to thermally seal tissue before any resection with liquid jet streams S1 and S2 is commenced. In such a method variation, the dual liquid jet streams then only resect tissue that has already been thermally treated and sealed. In another variation, the entire automated liquid jet resection is performed and thereafter, a vapor jet stream V is delivered for a selected time interval to accomplish the cauterization step. In yet another variation, the liquid jet resection and delivery of vapor streams V is sequential, with a liquid jet resection interval of 5 seconds to 30 seconds followed by vapor jet delivery for 5 to 30 seconds, with the intervals repeated multiple times until the targeted volumetric reduction is achieved, In another variation, the liquid jet streams S1, S2 and the vapor jet streams V are delivered contemporaneously with the vapor jet stream cauterizing tissue surface during the resection. In this variation, the liquid jet streams S1, S2 will cause some quenching of the vapor jet streams such that high vapor flow rates may be required.

Figure 14D:
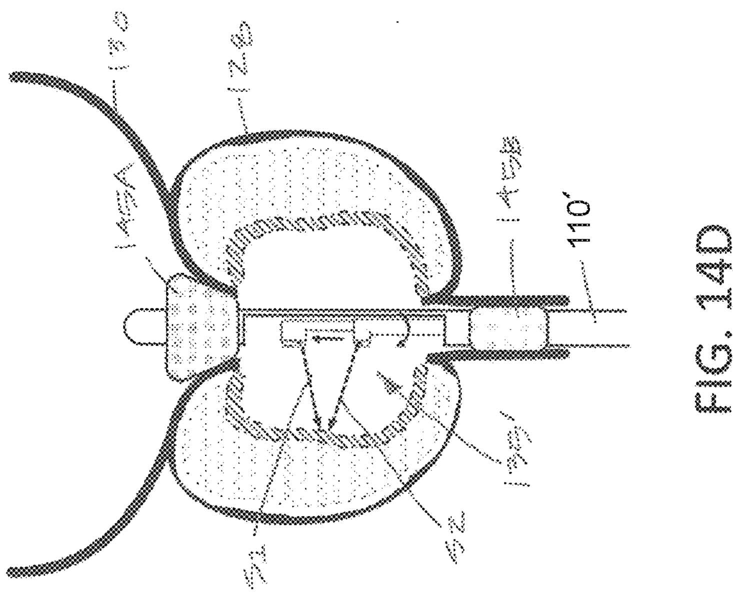
FIG. 14D is a subsequent step repeating the step of FIG. 14B, wherein the dual liquid jet assembly is adjusted for deeper resection and actuated to resect the tissue in the coagulated zone around the resected cavity.
Figure 14C:
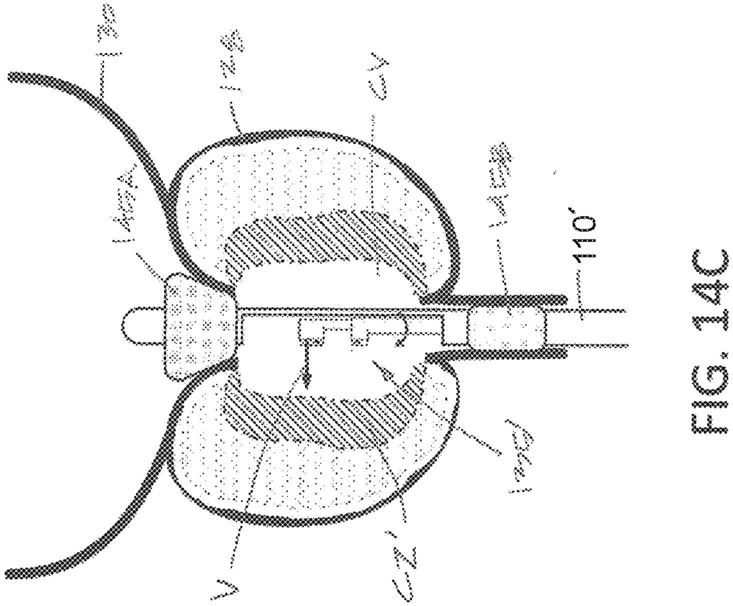
FIG. 14C is a subsequent step repeating the step of FIG. 14A, wherein the vapor delivery system is again actuated to provide a vapor jet stream to coagulate a tissue zone outward from the resected cavity.

An exemplary the method variation is shown in FIGS. 14A-14D. In FIG. 14A, it can be seen that the resection-coagulation device shaft 110' is positioned within the prostatic urethra 126 and a vapor stream V is delivered for 10 to 60 seconds, or often from 10 to 30 seconds, to provide a coagulated sone CZ of tissue surrounding the prostatic urethra 126. FIG. 14B then illustrated a subsequent step that provides the dual liquid streams S1, S2 to resect and extract the cauterized tissue, wherein the robotic control automatically resects to a predicted depth of the coagulation. FIG. 14C then depicts a subsequent step where a vapor jet stream V again coagulates another region CZ' outward from resected cavity CV. FIG. 14D next depicts the adjustment of the spaced apart liquid jet streams S1, S2 to cut deeper, and then again the automated resection is performed to resect tissue in the coagulated zone CZ'. The sequence of steps can be repeated until the planned volumetric reduction is achieved.

In another aspect of the invention, the automated robotic resection is assisted with artificial intelligence (AI) and/or machine learning. The controller 215 is provided with algorithms adapted to monitor video imaging from the device's image sensor 265 (FIG. 10) and image processor in real-time to identify selected site characteristics or site artifacts within view of the image sensor 265. In response to observation of a selected characteristic or artifacts, the controller 215 automatically modulates or terminates an operating parameter of the system, wherein examples of operating parameters are actuation of the liquid jet streams, pressure of each liquid jet stream, spacing of liquid jet streams, actuation of a vapor jet stream, adjustment of cal/sec delivered by the vapor jet stream, movement of the resecting assembly, operation of negative pressure source, and adjustment of the position of the robotic arm.

The site characteristics or artifacts that the AI or machine learning algorithms monitor are, at a minimum: image observable colors that indicate bleeding, observable bubbles in images that indicate cavitation, observable collapse of side walls of the resection cavity, observable tissue debris that indicates sub-optimal cutting, color of tissue indicating cauterization or coagulation, tissue features indicating prostate tissue types, and identification of verumontanum, ducts and other distinguishing features of a prostate.

Figure 15:
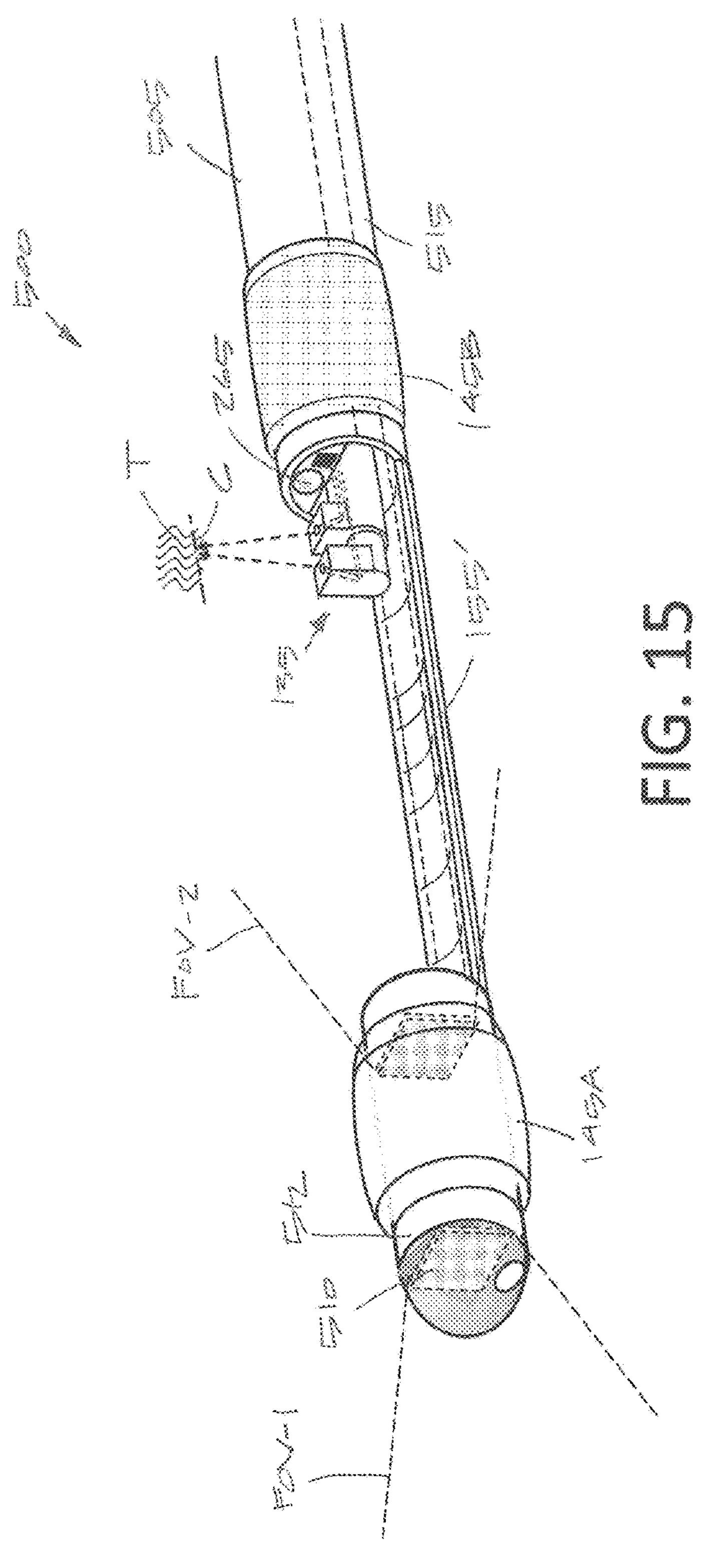
FIG. 15 is a perspective view of another variation of a working end similar to that of FIG. 4B, except the distal tip carries a distal facing image sensor providing a distal field of view for introducing the shaft into the prostatic urethra and an optional proximal facing image sensor providing a field of view for viewing the resecting assembly during a procedure.
Figure 16:
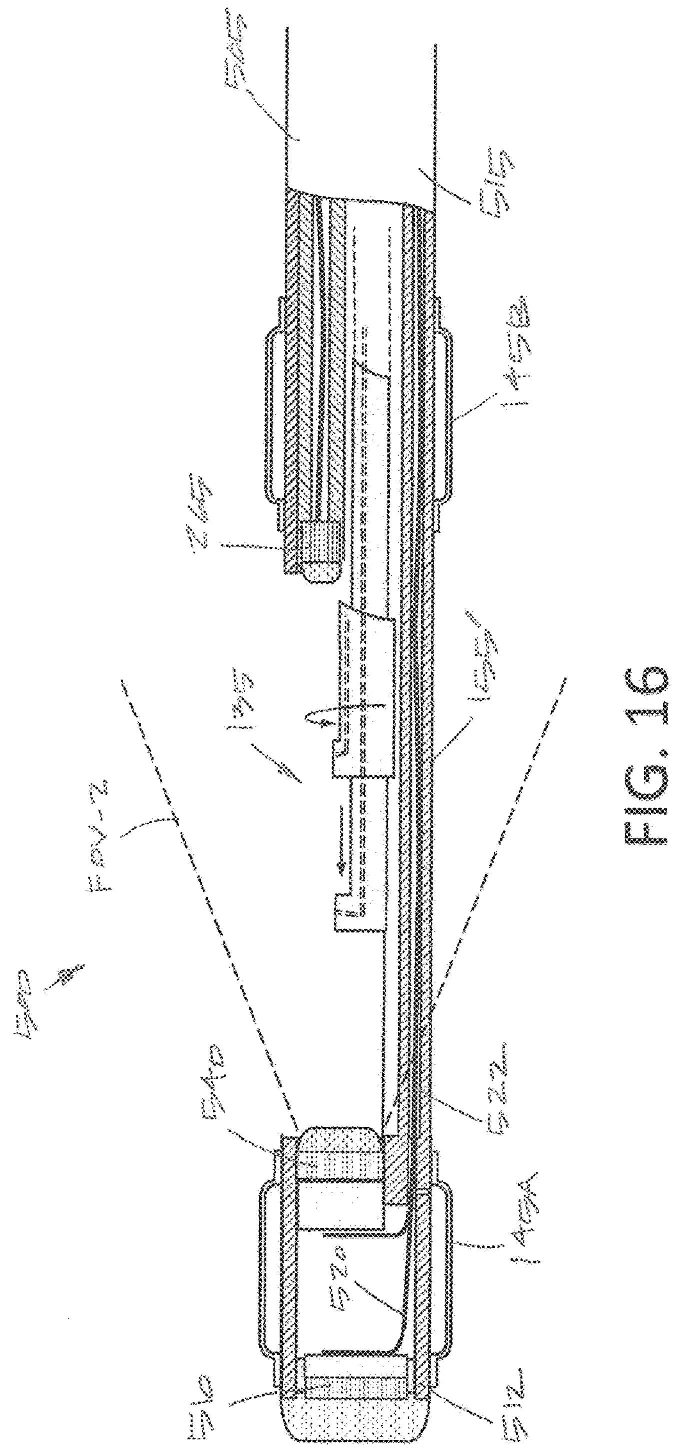
FIG. 16 is a cut-away view of the working end of FIG. 15.

FIGS. 15 and 16 illustrate another variation of the working end of a resection device 500, which is similar to the working end of FIG. 4B above. The variation of FIG. 15 includes an image sensor 510 in the distal tip 512 of the elongated shaft 515, which thus eliminates the need for a removable endoscope 180 of the type shown in FIG. 6. In FIG. 15, the distal tip 512 can accommodate a large image sensor, for example, an image sensor that is 4 mm to 5 mm in diagonal dimension, providing field of view FOV-1. Such large image sensors 510 are inexpensive and can be connected to the hub or housing 108 (e.g., FIG. 8) with a flex circuit 520 in a passageway 522 in the axially extending section 155' of the working end of the resection device 500 (FIG. 16). An irrigation movement can also be provided to extend through the actually extending section of the working end of the resection device 500. In a related variation, a second image sensor 540 with field of view FOV-2 optionally can be provided in the distal tip 512 that views in the proximal direction towards the jet resection assembly 135. Again, an inexpensive large image sensor 540 can be coupled to the flex circuit 520. The second image sensor 540 can be used in conjunction with originally-described image sensor 265 shown in FIGS. 15 and 16.

Figure 17:
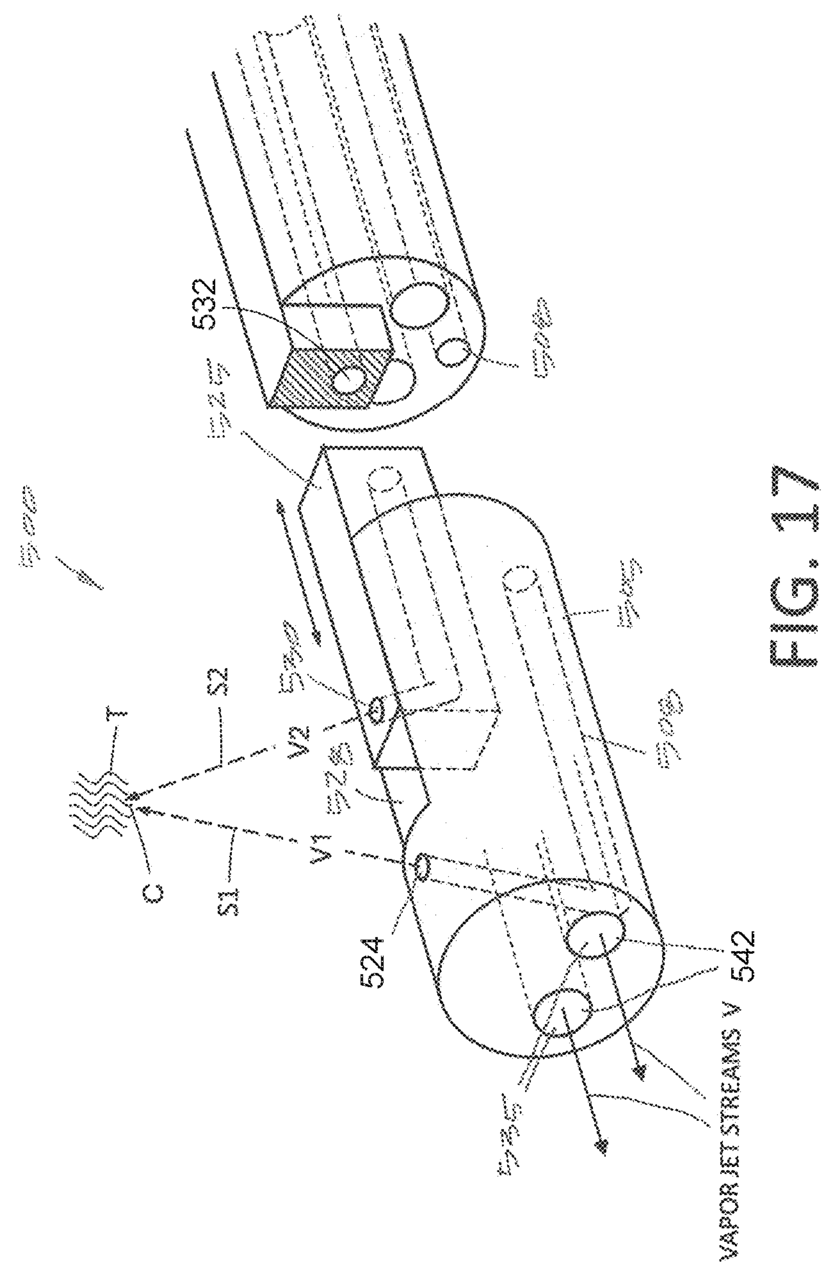
FIG. 17 is a partial sectional view of another variation of an integrated resection-cauterization assembly separated from the device shaft.

FIG. 17 illustrates another variation of resecting-cauterizing assembly 500 that functions as the assembly 135' of FIG. 12 but has a smaller profile. The assembly 500 in FIG. 17 has a shaft member 505 with a first flow channel 508 therein that extends to the first jet orifice 524. The flow channel 508 and jet orifice 524 are again angled to propagate a liquid jet stream S1 in vector V1 outwardly from the shaft. In the variation of FIG. 17, a second member 525 is slidable within an axial slot 528 in the shaft member 505. The second member 525 has a second flow channel 532 therein that extends to the second jet orifice 530 for propagating liquid jet stream S2 in vector V2. A robotically controlled motor drive, as described previously, is configured to move the second member 525 to adjust the spacing between the first jet orifice 524 and the second jet orifice 530 as in previous variations. In FIG. 17, two additional channels 535 are provided for vapor flow to the vapor outlet 542 which faces distally, but any direction is possible. The vapor channels 535 are positioned on either side of the first flow channel 508 as a means for saving space in the shaft assembly. In all other respects, the resection and cauterizing assembly 500 functions as described in previous variations. In the variation of FIG. 17, the shaft 505 and the slidable second member 525 may be fabricated or extruded of a polymeric material to reduce manufacturing costs.

The above methods have been described with reference to cauterizing prostate tissue after tissue removal to treat BPH, but it should be appreciated that other prostate treatments may require tissue resection followed by cauterization, such as a prostate cancer treatment.

The methods described above refer to the use of condensable water vapor, but other vaporizable liquids may be used, such as vaporized saline or vaporized alcohol.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications and patents cited herein are hereby incorporated by reference as if set forth in its entirety herein.

What is claimed is:

1. A method of liquid jet cutting of soft tissue, comprising:

providing a working end of a shaft of a tissue cutting device with a first member having a first flow channel configured to propagate a first liquid jet stream outwardly in a first vector and a second member having a second flow channel configured to propagate a second liquid jet stream outwardly in a second vector;

positioning the working end in an interface with a targeted tissue; and propagating the first liquid jet stream and the second liquid jet stream outwardly at selected pressure parameters that provide kinetic energy in the first liquid jet stream and the second liquid jet stream to cut the targeted tissue;

wherein the first vector and the second vector converge at an outward point of convergence to thereby induce turbulence adapted to dissipate the kinetic energy of the first liquid jet stream and the second liquid jet stream to control a cutting depth; and adjusting the outward point of convergence during an interval of propagating the first liquid jet stream and the second liquid jet stream.

2. The method of claim 1, wherein the first vector and the second vector extend outwardly from an axis of the shaft at an angle ranging from 30° to 90°.

3. The method of claim 1, wherein the outward point of convergence is outward from an axis of the shaft from 5 mm to 25 mm.

4. The method of claim 1, further comprising moving the first liquid jet stream and the second liquid jet stream at least one of helically, rotationally or axially during an interval of propagating the first liquid jet stream and the second liquid jet stream.

5. The method of claim 4, wherein moving the first liquid jet stream and the second liquid jet stream is provided by a motor drive that moves the working end.

6. The method of claim 1, wherein adjusting the outward point of convergence comprises using a motor drive that adjusts a spacing between a first jet orifice and a second jet orifice that propagate the first liquid jet stream and the second liquid jet stream respectively.

7. The method of claim 1, further comprising propagating a vapor jet from the working end, wherein a subsequent vapor-to-liquid phase transition applies cauterizing energy to the targeted tissue.

8. The method of claim 7, wherein propagating the vapor jet occurs before propagating the first liquid jet stream and the second liquid jet stream.

9. The method of claim 7, wherein propagating the vapor jet occurs contemporaneously with propagating the first liquid jet stream and the second liquid jet stream.

10. The method of claim 7, wherein propagating the vapor jet and propagating the first liquid jet stream and the second liquid jet stream are done sequentially.

11. The method of claim 7, wherein propagating the vapor jet occurs after propagating the first liquid jet stream and the second liquid jet stream to cut a volume of the targeted tissue.

12. The method of claim 1, further comprising actuating a negative pressure source communicating with the working end to extract tissue debris and liquid after the first liquid jet stream and the second liquid jet stream cut a volume of the targeted tissue.

13. A medical system for liquid jet cutting and cauterization of soft tissue, comprising:

a housing coupled to an elongate shaft configured for trans-urethral introduction to a patient's prostatic urethra;

a working end of the elongate shaft including a first jet orifice configured to propagate a first liquid jet stream outwardly in a first vector and a second jet orifice configured to propagate a second liquid jet stream outwardly in a second vector wherein the first vector and the second vector converge at a point of convergence outward from an axis of the working end;

a controller coupled to a motor drive configured to adjust an axial spacing between the first jet orifice and the second jet orifice; and a vapor jet outlet in the working end configured to propagate a vapor jet stream outwardly from the working end.

14. The medical system of claim 13, further comprising at least one motor drive operated by the controller to move the working end at least one of helically, rotationally and axially.

15. The medical system of claim 13, wherein the first vector and the second vector extend outwardly from the axis of the working end at angle ranging from 30° to 90°.

16. The medical system of claim 13, wherein the point of convergence is outward from the axis of the working end from 5 mm to 25 mm.

17. The medical system of claim 13, further comprising a negative pressure source communicating with the working end configured to extract tissue debris and liquid from a treatment site.

18. The medical system of claim 17, wherein the controller is configured to control an extraction outflow to maintain pressure in a selected pressure range in the treatment site.

19. The medical system of claim 13, wherein the elongate shaft carries first and second occlusion members for positioning proximally and distally of a prostatic urethra.

20. A method of liquid jet cutting of soft tissue, comprising:

providing a working end of a shaft of a tissue cutting device with a first member having a first flow channel configured to propagate a first liquid jet stream outwardly in a first vector and a second member having a second flow channel configured to propagate a second liquid jet stream outwardly in a second vector;

positioning the working end in an interface with a targeted tissue; and propagating the first liquid jet stream and the second liquid jet stream outwardly at selected pressure parameters that provide kinetic energy in the first liquid jet stream and the second liquid jet stream to cut the targeted tissue;

wherein the first vector and the second vector converge at an outward point of convergence to thereby induce turbulence adapted to dissipate the kinetic energy of the first liquid jet stream and the second liquid jet stream to control a cutting depth, and adjusting an axial spacing between the first liquid jet stream and the second liquid jet stream to adjust the outward point of convergence.

21. The method of claim 20, further comprising propagating a vapor jet from the working end, wherein a subsequent vapor-to-liquid phase transition applies cauterizing energy to the targeted tissue.

22. The method of claim 21, wherein propagating the vapor jet occurs before propagating the first liquid jet stream and the second liquid jet stream.

23. The method of claim 21, wherein propagating the vapor jet occurs contemporaneous with propagating the first liquid jet stream and the second liquid jet stream.

24. The method of claim 21, wherein propagating the vapor jet and propagating the first liquid jet stream and the second liquid jet stream are done sequentially.

25. The method of claim 21, wherein propagating the vapor jet occurs after propagating the first liquid jet stream and the second liquid jet stream to cut a volume of the targeted tissue.

* * * * *